United States Patent
He

(10) Patent No.: US 9,733,326 B2
(45) Date of Patent: Aug. 15, 2017

(54) SELECTIVE ZERO-QUANTUM COHERENCE TRANSFER (SEL-ZQC) METHOD FOR METABOLITE IMAGING IN A POORLY SHIMMED MAGNET FIELD WITHOUT SUSCEPTIBILITY ARTIFACT

(75) Inventor: Qiuhong He, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 982 days.

(21) Appl. No.: 14/004,624

(22) PCT Filed: Apr. 9, 2012

(86) PCT No.: PCT/US2012/032739
§ 371 (c)(1),
(2), (4) Date: Nov. 5, 2013

(87) PCT Pub. No.: WO2012/139104
PCT Pub. Date: Oct. 11, 2012

(65) Prior Publication Data
US 2014/0296695 A1    Oct. 2, 2014

Related U.S. Application Data

(63) Continuation of application No. 13/501,000, filed as application No. PCT/US2011/032691 on Apr. 15, (Continued)

(51) Int. Cl.
*G01V 3/00* (2006.01)
*G01R 33/485* (2006.01)
(Continued)

(52) U.S. Cl.
CPC ............ *G01R 33/485* (2013.01); *A61B 5/055* (2013.01); *A61B 5/4064* (2013.01);
(Continued)

(58) Field of Classification Search
CPC .................................................. G01R 33/4608
(Continued)

(56) References Cited

U.S. PATENT DOCUMENTS

| 4,680,546 A * | 7/1987 | Dumoulin ........... G01R 33/4828 324/300 |
| 4,774,467 A * | 9/1988 | Sorensen ........... G01R 33/4633 324/309 |

(Continued)

OTHER PUBLICATIONS

Notification of Transmittal of the International Search Report and the Written Opinion of the International Searching Authority, or the Declaration, Dec. 20, 2012, 8 pages.

*Primary Examiner* — Louis Arana
(74) *Attorney, Agent, or Firm* — Eckert Seamans Cherin & Mellott, LLC; Philip E. Levy

(57) ABSTRACT

Systems and methods employing spin editing techniques to improve magnetic resonance spectroscopy (MRS) and magnetic resonance spectroscopic imaging (MRSI) are discussed. Using these spin editing techniques, magnetic resonance signals of one or more non-target chemicals (chemicals whose signals are to be filtered out or suppressed) chemicals can be suppressed, so that the signal(s) of a set of target chemicals can be obtained without signals from the one or more non-target chemicals. Information about and differences between the molecular topologies of the first set of chemicals and the one or more unwanted chemicals can be used to design a sequence that suppresses the one or more unwanted chemicals while allowing acquisition of signal(s) from the first set of chemicals. These techniques can be employed to recover sharp peaks despite magnetic field inhomogeneities and susceptibility effects.

20 Claims, 15 Drawing Sheets

Related U.S. Application Data 2011, now Pat. No. 9,285,443, and a continuation-in-part of application No. 12/266,007, filed on Nov. 6, 2008, now Pat. No. 8,731,635.

(60) Provisional application No. 61/473,648, filed on Apr. 8, 2011, provisional application No. 61/324,796, filed on Apr. 16, 2010, provisional application No. 60/986,253, filed on Nov. 7, 2007.

(51) Int. Cl.
*A61B 5/055* (2006.01)
*A61B 5/00* (2006.01)
*G01R 33/46* (2006.01)
*G01R 33/34* (2006.01)
*G01R 33/341* (2006.01)
*G01R 33/3415* (2006.01)
*G01R 33/36* (2006.01)
*G01R 33/565* (2006.01)

(52) U.S. Cl.
CPC ........ *A61B 5/4312* (2013.01); *G01R 33/4608* (2013.01); *G01R 33/341* (2013.01); *G01R 33/3415* (2013.01); *G01R 33/34046* (2013.01); *G01R 33/3635* (2013.01); *G01R 33/4633* (2013.01); *G01R 33/56536* (2013.01)

(58) Field of Classification Search
USPC .......................................... 324/307, 309, 314
See application file for complete search history.

(56) References Cited

U.S. PATENT DOCUMENTS

| | | | |
|---|---|---|---|
| 6,046,588 | A | 4/2000 | Watanabe |
| 6,373,250 | B1 | 4/2002 | Tsoref et al. |
| 6,528,997 | B2 | 3/2003 | Zhong et al. |
| 6,696,889 | B2 | 2/2004 | Watanabe |
| 9,285,443 | B2 * | 3/2016 | He .................... G01R 33/1284 |
| 2009/0039883 | A1 * | 2/2009 | Bodenhausen ........ G01R 33/46 324/307 |

* cited by examiner

SELECTIVE ZERO-QUANTUM COHERENCE TRANSFER (SEL-ZQC) METHOD FOR METABOLITE IMAGING IN A POORLY SHIMMED MAGNET FIELD WITHOUT SUSCEPTIBILITY ARTIFACT

CROSS-REFERENCE TO RELATED APPLICATIONS

This application claims the benefit of U.S. Provisional Patent application Ser. No. 61/473,648 entitled 'Selective Zero-Quantum Coherence Transfer (Sel-ZQC) Method for Metabolite Imaging in a Poorly Shimmed Magnet Field' and filed Apr. 8, 2011 and is a Continuation-in-Part of U.S. patent application Ser. No. 13/501,000 entitled 'SIMULTANEOUS MAPPING OF MULTIPLE CHEMICALS WITH SUPPRESSION OF UNWANTED SIGNALS VIA MOLECULAR SPECIFIC COHERENCE (MSC)-SELMQC (SELECTIVE MULTIPLE QUANTUM COHERENCE)' and filed Apr. 9, 2012, which claims the benefit of U.S. Provisional Application Ser. No. 61/324,796 filed on Apr. 16, 2010, entitled "MSC-SELMQC METHOD FOR SIMULTANEOUS MAPPING OF POLYUNSATURATED FATTY ACIDS, LACTATE AND CHOLINE IN HIGH FAT TISSUES." and International Application Serial No. PCT/US11/32691 filed on Apr. 15, 2011, and is a Continuation-in-Part of pending U.S. patent application Ser. No. 12/266,007 filed on Nov. 6, 2008 and entitled "COILS FOR MAGNETIC RESONANCE SPECTROSCOPY AND IMAGING OF HUMAN BREAST," which claims the benefit of U.S. Provisional Application Ser. No. 60/986,253 filed on Nov. 7, 2007, entitled "COILS FOR MAGNETIC RESONANCE SPECTROSCOPY AND IMAGING OF HUMAN BREAST AT HIGH MAGNETIC FIELD.". The entireties of the above-noted applications are incorporated by reference herein.

NOTICE ON GOVERNMENT FUNDING

This invention was made with government support under grant # CA109471 awarded by the National Institutes of Health (NIH). The government has certain rights in the invention.

BACKGROUND

Magnetic resonance imaging and spectroscopy are non-invasive techniques that allow probing of soft and hard tissue in humans. In addition to being used as diagnostic tools, magnetic resonance imaging (MRI) and magnetic resonance spectroscopy (MRS) can be utilized in interventional procedures. While proton ($^1$H) MRS and MRI has been employed extensively in brain cancer studies, substantially less research and development has succeeded in extracranial cancer research (particularly breast cancer research) through magnetic resonance spectroscopy, in particular at high magnetic fields (e.g., at or above 3 T), in part because of the relative ease of intracranial MRS as compared with extracranial, even though brain cancer has a relatively low incidence compared to some other types of cancer. For example, breast cancer is the most common malignancy and the number-one leading cause of cancer-related death in women. Each year, nearly 465,000 patients die from breast cancer worldwide, and 1,302,000 more women are newly diagnosed with this disease. Due to its relative good prognosis, nearly 4.4 million breast cancer survivors are living today; however, incidence rates of breast cancer are increasing in most countries. Mortality of breast cancer is mostly associated with metastasis. The current therapeutic interventions typically have limited effect in the treatment of metastatic breast cancer and antiestrogen-chemo- and radiation-resistant tumors. Therefore, early detection is critical in breast cancer management.

A possible reason for having a lesser volume of breast cancer (and other extracranial cancer) research and clinical success through MRS is that several disparate techniques are mature and used customarily at the clinic level, even though such techniques have substantive limitations. For instance, one technique readily employed is mammography, yet mammography screening has a false positive rate about 70%-80%. Ultrasonography is another technique that is often utilized in conjunction with mammography; however, ultrasonography has lower specificity (i.e., more false positives) than mammography. Positron emission tomography/computed tomography (PET/CT) is another technique widely utilized and highly sensitive to detect cancer (e.g., breast cancer) and metastasis for tumors larger than 1 cm; sensitivity decreases significantly for smaller tumors.

Since its first observation about half a century ago, magnetic resonance spectroscopy (MRS) has evolved into a practical technique with a great impact on biology and medicine. It is highly sensitive to the chemical environment of biomolecules and has been used to solve three-dimensional (3D) protein structures and to probe protein dynamics and interactions in aqueous solutions. Magnetic resonance imaging (MRI) detects the tissue water signal for imaging the anatomical organ structures. Because it provides high-resolution anatomical images without the use of ionizing radiation, MRI is powerful in identifying neoplastic changes in soft tissues. The MRI sensitivity for cancer detection can be enhanced by the use of exogenous contrast agents.

Regarding MRS and MRI techniques as applied to breast cancer, proton MRS and MRI techniques can differentiate between benign and malignant breast lesions in vivo. MRI has a high sensitivity (typically greater than 99%) in detecting breast cancer, but low specificity (37%-86%) with a high false-positive rate; MRS can improve breast cancer detection specificity. Currently, choline has been typically the only metabolite that has been observed reliably in human breast cancer by proton MRS, reaching a sensitivity and improved specificity of tumor detection of approximately 78% and 86%, respectively.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, can include systems and methods capable of detecting magnetic resonance (MR) signals. These systems and methods can include a method of detecting magnetic resonance (MR) signals. Such a method can include the acts of exciting a set of target chemicals into a set of multiple-quantum (MQ) states and applying a gradient pulse to select zero-quantum coherences (ZQCs) of the set of target chemicals. Additionally, the method can include the steps of converting the ZQCs into a set of detectable magnetizations and acquiring signals from the set of target chemicals during an acquisition period.

In other embodiments, the innovation can comprise a magnetic resonance spectroscopic imaging (MRSI) system. The system can include a sample that comprises one or more target chemicals and one or more non-target chemicals, and a magnet that applies a B0 field to the one or more target chemicals and the one or more non-target chemicals. The system can also include an excitation/detection component that generates a sequence of pulses that excites the one or more target chemicals into a first set of multiple-quantum (MQ) states, selects a zero-quantum coherence (ZQC) of the one or more target chemicals, and converts the one or more target chemicals from the ZQC to a detectable magnetization. The excitation/detection component can acquire signals from the one or more target chemicals during an acquisition period.

The subject innovation, in an aspect, relates to spin editing techniques that can be used in systems and methods to improve magnetic resonance spectroscopy (MRS) and magnetic resonance spectroscopic imaging (MRSI). Using sequences and techniques discussed herein, magnetic resonance signals of one or more non-target chemicals (that is, chemicals whose signals are to be filtered out or suppressed) can be suppressed, so that the signal(s) of a target set of chemicals can be obtained without signals from the one or more non-target chemicals. Information about and differences between the molecular topologies of the first set of chemicals and the one or more non-target chemicals can be used to design a sequence that suppresses the one or more non-target chemicals while allowing acquisition of signal(s) from the first set of chemicals. As will be understood, these systems and methods can be used in a variety of settings, such as detecting low concentration signals, or resolving overlapping signals, in samples with high concentrations of non-target chemicals. In aspects, the subject innovation can be employed to recover magnetic resonance signals from the target set of chemicals unconfounded by magnetic field inhomogeneities or susceptibility effects.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
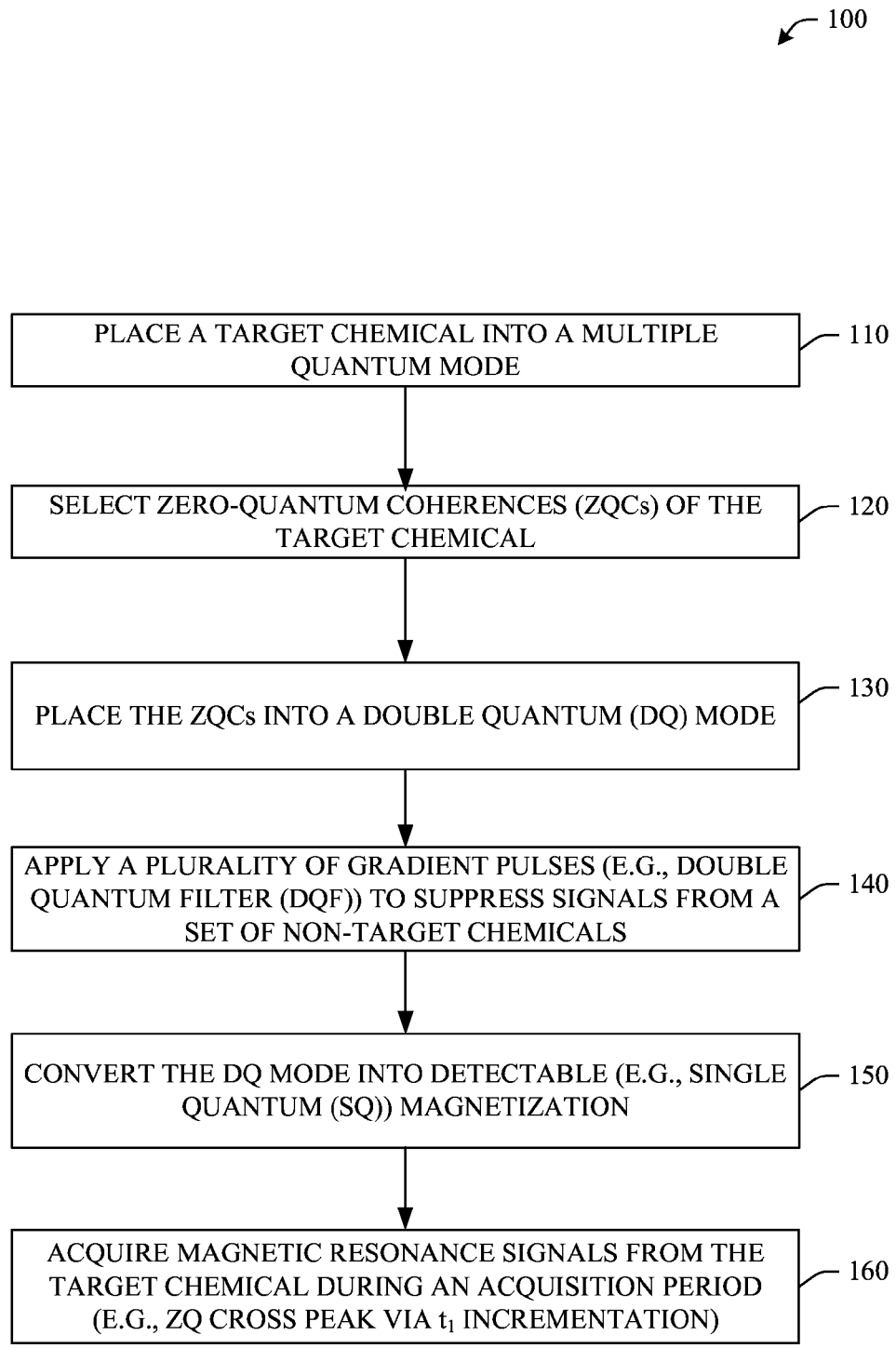
FIG. 1 illustrates a method of selectively obtaining magnetic resonance (MR) signals from a target chemical while suppressing non-target chemicals, in accordance with aspects of the subject innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, a "set" refers to a non-empty set unless specifically indicated otherwise, that is, a collection of one or more distinct elements. Moreover, articles "a" and "an" as used in the subject specification and annexed drawings should generally be construed to mean "one or more" unless specified otherwise or clear from context to be directed to a singular form.

Example methodologies that may be implemented in accordance with the disclosed subject matter will be better appreciated with reference to the flowcharts contained in the figures and described herein. While, for purposes of simplicity of explanation, the example methodologies are shown and described as a series of acts, it is to be understood and appreciated that the claimed subject matter is not limited by the number or order of acts, as some acts may occur in different orders and/or concurrently with other acts from what is depicted and described herein. Moreover, not all illustrated acts may be required to implement the methodologies described hereinafter. It is to be appreciated that the functionality associated with the acts may be implemented by software, firmware, hardware, a combination thereof or any other suitable means (e.g., device, system, process, component). Additionally, it should be further appreciated that the example methodologies disclosed hereinafter and throughout this specification can be stored on an article of manufacture to facilitate transporting and transferring such methodologies to various devices or computers for execution by a processor or for storage in a memory. It should be understood and appreciated that a methodology could alternatively be represented as a series of interrelated states or events, such as in a state diagram or call flow.

The subject innovation, in an aspect, relates to spin editing techniques that can be used in systems and methods to improve magnetic resonance spectroscopy (MRS) and magnetic resonance spectroscopic imaging (MRSI). Using sequences and techniques discussed herein, magnetic resonance signals of one or more non-target nuclei (e.g., from chemicals whose signals are to be filtered out or suppressed) can be suppressed, so that the signal(s) of a first set of target nuclei (or nuclei of interest) can be obtained without signals from the one or more non-target nuclei. Information about and differences between the molecular topologies of the first set of target nuclei and the one or more non-target nuclei can be used to design a sequence that suppresses the one or more non-target nuclei while allowing acquisition of signal(s) from the first set of target nuclei. As will be understood, these systems and methods can be used in a variety of settings, such as detecting low concentration signals in samples with high concentrations of non-target chemicals, in homo- or heteronuclear MRS experiments.

Conventional magnetic resonance spectroscopic imaging in human scanners at ultrahigh magnetic field encounters numerous technical challenges. For example, gradient hardware for whole-body shimming of magnetic field inhomogeneity is not widely available at human 7T and 9.4T scanners, which traditionally has limited the ability to generate high quality NMR spectra in vivo due to magnetic susceptibility artifacts. In aspects, the subject innovation relates to systems and methods of zero-quantum spin editing such as Selective Zero-Quantum Coherence Transfer (Sel-ZQC) and related techniques, which can provide high-resolution spectroscopic imaging of metabolite distributions even in a poorly shimmed magnetic field and in the presence of strong tissue magnetic susceptibility effect. These techniques are related to selective multiple quantum coherence transfer techniques described herein. In Sel-ZQC, the Zero-Quantum (ZQ)-spectra of metabolites are not subject to magnetic susceptibility artifacts with ultrahigh field human MRI scanners, giving the capability to generate high quality spectra and scans even in poorly shimmed magnetic fields. Using a double quantum filter (DQF), the Sel-ZQC sequence can maintain complete lipid and water suppression.

Turning to FIG. 1, in accordance with various aspects of the subject innovation, illustrated is a method 100 of selectively obtaining magnetic resonance (MR) signals from a target chemical while suppressing non-target chemicals. Method 100 can include exciting at least two sets of nuclei of the target chemical into a multiple quantum (MQ) mode at 110, as described in greater detail herein. At 120, zero-quantum coherences (ZQCs) of the target chemical can be selected. Next, at 130, the set of ZQCs can be converted into a double quantum (DQ) mode, which can be used for later suppression of signals from unwanted or non-target chemicals. Optionally, at 140 the method can apply a plurality of gradient pulses (e.g., a double quantum filter (DQF) gradient) to suppress signals from a set of non-target chemicals. The plurality of gradient pulses can be designed to selectively remove signals for the set of chemicals to be filtered out. These gradient pulses can be designed based on known information about the first set of chemicals, the second set of chemicals (if they are to be measured), and the set of chemicals to be filtered out (alternatively referred to as "non-target" chemicals, compounds, molecules, signals, etc., or referred to as chemicals, compounds, molecules, signals, etc. to be removed). These differences can be based on differences in chemical shift between the compounds when exposed to an external magnetic field $B_0$, and can be determined based on known characteristics of the molecular topologies involved. In an example embodiment discussed further herein, the plurality of gradient pulses can comprise a double quantum filter (DQF) gradient, e.g., two gradient pulses $g_1$ and $g_2$ in the ratio $g_1:g_2=-1:2$. The non-target chemicals can include chemicals that may in conventional situations obscure or overwhelm the signal from the target chemical, and can include lipids or water, both of which may be present in large quantities in extracranial organs, for example. Also, at 150, which can occur contemporaneously with step 140, the DQ mode can be converted into a detectable magnetization (e.g., single quantum (SQ)). Next, at 160, magnetic resonance signals can be acquired from target chemical, such as obtaining a zero-quantum (ZQ) cross peak indirectly via multiple acquisitions at constant increment along a ZQ-evolution time $t_1$. Because of the use of the ZQC, as explained in greater detail herein, the effects of magnetic field inhomogeneities or magnetic susceptibility are reduced, and a sharp peak can be recovered.

Figure 2:
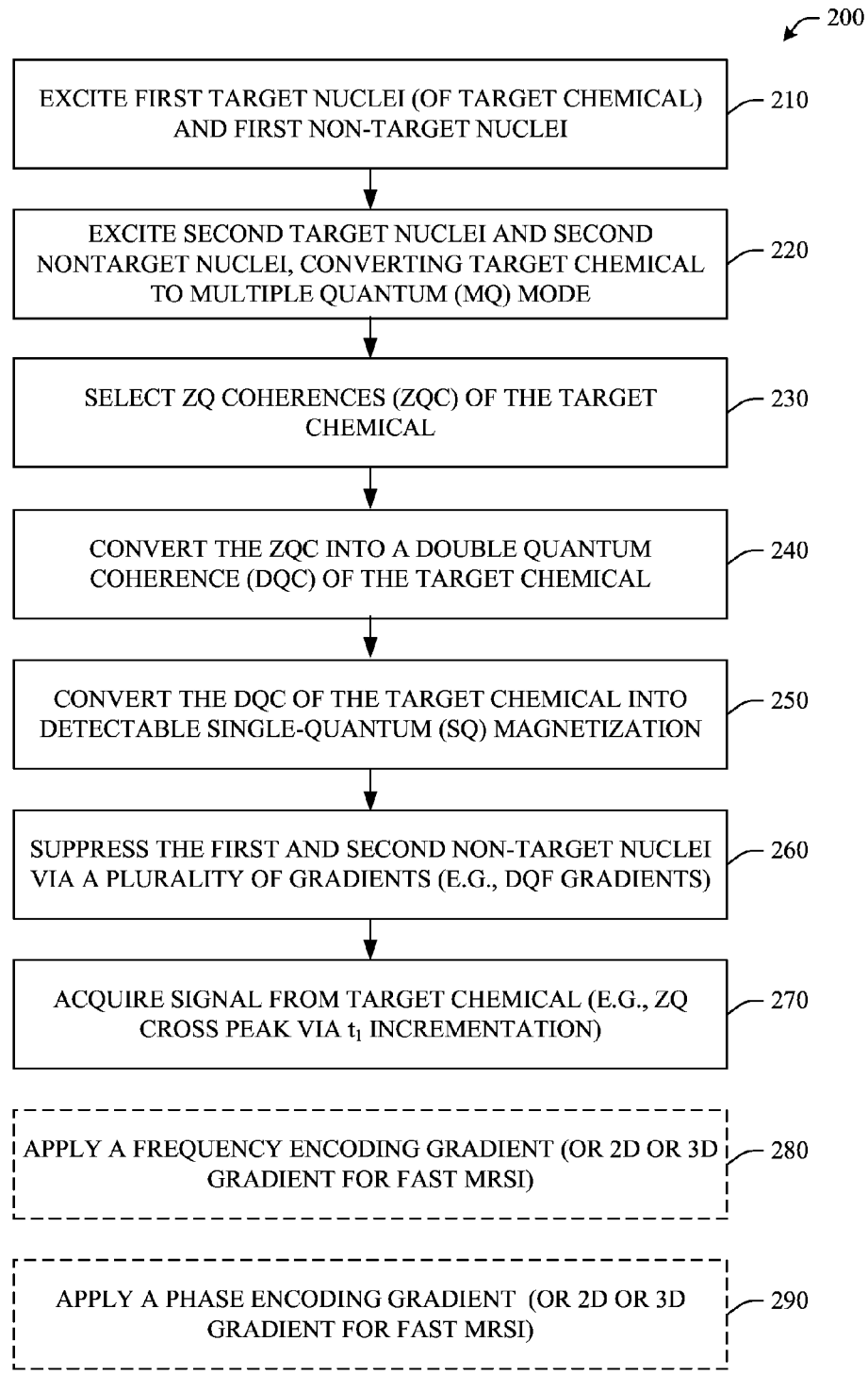
FIG. 2 illustrates an example method of acquiring MR signals from a target chemical in accordance with aspects of the subject innovation.
Figure 3:
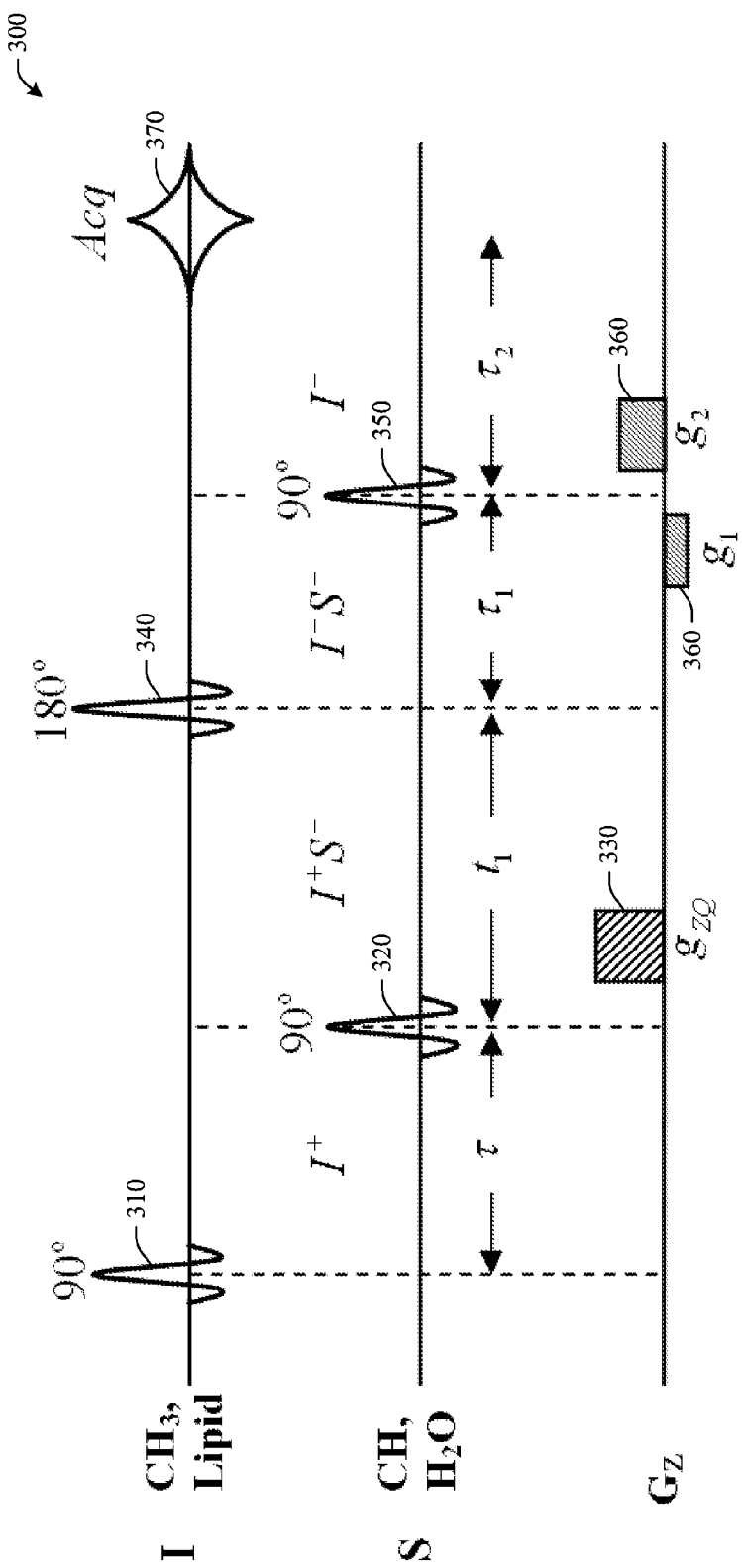
FIG. 3 illustrates an example selective zero-quantum coherence transfer (Sel-ZQC) pulse sequence for acquiring the high-resolution zero-quantum nuclear magnetic resonance (ZQ-NMR) spectra of lactate.

FIG. 2 illustrates an example method 200 of acquiring MR signals from a target chemical in accordance with aspects of the subject innovation. Method 200 is described in connection with an example application to lactate as the target chemical in order to provide a concrete example, although it is to be understood in light of the teachings herein that the methods described in connection with the subject innovation can be employed in other contexts, such as with other target chemicals, other non-target chemicals, etc. Additionally, method 200 can be understood in connection with FIGS. 3 and 4, which illustrate, respectively, Sel-ZQC pulse sequences 300 and 400 for acquiring the high-resolution ZQ-NMR spectra (sequence 300) and imaging metabolite distributions (sequence 400). Since ZQ-coherences are not sensitive to magnetic field inhomogeneity or magnetic susceptibility effects, the subject innovation can employ these sequences to measure spectra of one or more biochemicals in human tissues in vivo with high field magnets (e.g., 7T and 9.4T human MRI scanners), which are usually not equipped with whole-body shimming hardware.

In connection with the above-described example, in lactate detection using a Sel-ZQC method such as method 200, the lactate $CH_3$ protons at 1.3 ppm (or other first target nuclei at the appropriate chemical shift, e.g., of polyunsaturated fatty acid (PUFA) or other chemicals described herein) can be selectively excited at 210, 310 or 410 by the first 90° pulse in channel I, which can also excite lipid at 1.3 ppm (or other first non-target nuclei at the corresponding chemical shift). In channel S, the selective 90° pulse at 220, 320, or 420 can excite the lactate CH at 4.2 ppm (or other second target nuclei at the appropriate chemical shift) and water protons at 4.7 ppm (or other second non-target nuclei at the corresponding chemical shift) after the MQ-preparation period $\tau=1/2J$ and converts the lactate anti-phase magnetization into the MQ-modes. In the subsequent ZQ-evolution period, $t_1$, zero-quantum coherences of lactate can be selected at 230, 330, or 430 by the ZQ-gradient, $g_{ZQ}$, which can dephase other spin coherences of lactate (or other target chemical) and lipid and water (or other non-target chemicals) remaining in the SQ-modes. A selective 180° pulse can be applied at 240, 340, or 440 on lactate $CH_3$ (or other second target nuclei), which can convert the ZQC into the DQC of lactate, and a final CH-selective 90° pulse (or selective of another first target nuclei) can be applied at 250, 350, or 450, which can convert the lactate DQ coherence into the detectable single-quantum (SQ) magnetization.

Figure 4:
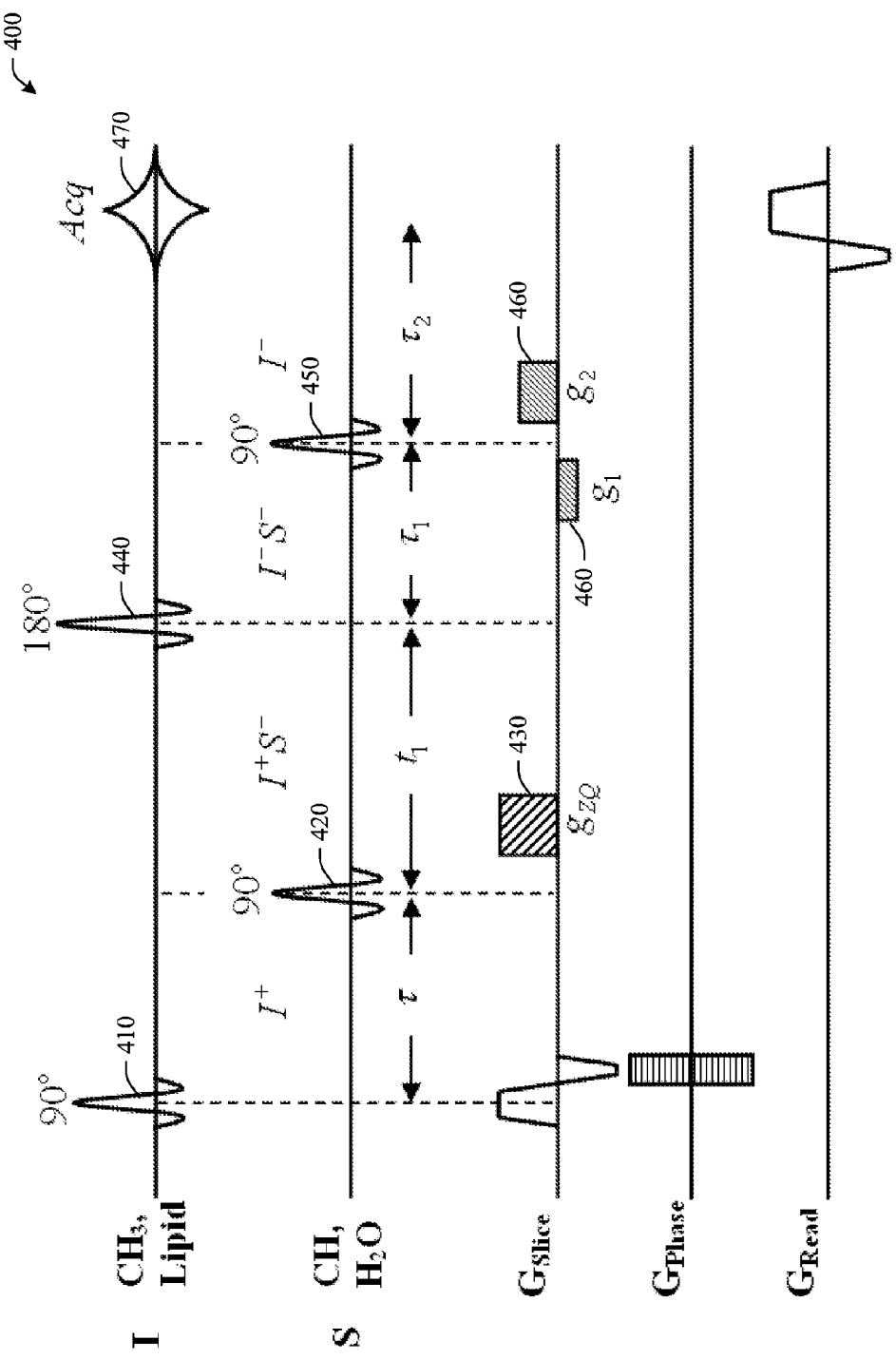
FIG. 4 illustrates an example Sel-ZQC pulse sequences for imaging metabolite distributions of lactate.

Water and lipid (or other non-target chemicals) suppression can be accomplished by a pair of double quantum filter (DQF) gradients ($g_1:g_2=-1:2$) at 260, 360, or 460 after a fixed DQ evolution time. The method can conclude at 270, 370, or 470 by acquiring MR signals from the target chemical, which can include acquiring a ZQ cross peak of the target chemical at the difference frequency of the first and second target nuclei (for lactate, of the $CH_3$ and CH proton chemical shifts at 1.3 and 4.1 ppm) via taking multiple measurements over time based on incrementation in $t_1$. In a poorly shimmed magnet, although the directly detected signal in $F_2$ dimension is sensitive to the magnetic field inhomogeneous broadening and susceptibility distortions with a total $B_o$ field shift of $\Delta B$, the ZQ resonances in the indirectly detected dimension $F_1$ occurring at the chemical shift differences between spin I and S, $\Omega_I-\Omega_S=(\omega_I+\gamma\Delta B)-(\omega_S+\gamma\Delta B)=\omega_I-\omega_S$ are not affected. Therefore, the frequency shifts (i.e., $\gamma\Delta B$) for both spin I and S in inhomogeneous field can be cancelled for ZQCs in $F_1$ dimension. In Sel-ZQC imaging, a frequency-encoding gradient at 280 and a phase encoding gradient at 290 can be applied to map metabolite spatial distributions, as shown in FIG. 4. In fast MRSI experiments, the two- or three-dimensional k-space may also be mapped using a tailored gradient waveform (e.g. spiral gradient or echo-planar gradient train) to replace the frequency- and phase-encoding gradients shown at 280 and 290.

Differently from other chemical shift imaging (CSI) experiments described herein, the chemical shift information of tissue metabolites via Sel-ZQC can be obtained in the indirectly detected ZQ-dimension by $t_1$ incrementation.

Systems and methods of the subject innovation, as well as experimental results and techniques discussed herein, relate to magnetic resonance spectroscopy (MRS) or chemical shift imaging (CSI), and associated conventions, notations, and nomenclature. Some results, system components, or method steps (for example, graphs of frequency response of molecules) may be presented in terms of chemical shift or in parts per million (ppm) relative to a reference frequency, as such measurements are independent of the amplitudes of the external magnetic field, $B_0$ (alternatively, they may also be expressed in terms of units for energy or frequency, e.g., hertz (Hz)). Chemical shift provides information about the environment of a nucleus (e.g., $^1H$, $^{23}Na$, $^{13}C$, etc.) to which coil resonance is tuned, because local geometry (e.g., properties of nearby chemical bonds, such as bond length, bond angle, binding partners, etc.) can cause changes in the energy levels of the nucleus, as the geometry varies the effective magnetic field acting on the nucleus (e.g., because of magnetic fields induced by nearby electrons). This change in energy levels, and hence resonance frequencies, is called chemical shift and is typically described in terms of a fractional change in frequency when compared to a reference, and commonly measured in ppm. Different nuclei in the same molecule can, in general, have different local geometry, and thus different resonant frequencies. Differences and similarities in these factors can contribute to variations in spectra for different chemicals. Healthy tissue, for example, can have certain concentrations of chemicals, each chemical with a specific profile or spectrum of chemical shifts. The set of chemicals in cancerous environments are mostly the same as in healthy tissue, and thus can exhibit mostly the same chemical shift spectrum, but concentrations of each chemical in the set of chemicals are different than in healthy tissue. Accordingly, chemical shift intensity measurements can reveal different profiles of intensity affected primarily by concentration of chemicals, wherein the concentration can be affected by compounds present in cancerous tissue.

Figure 5:
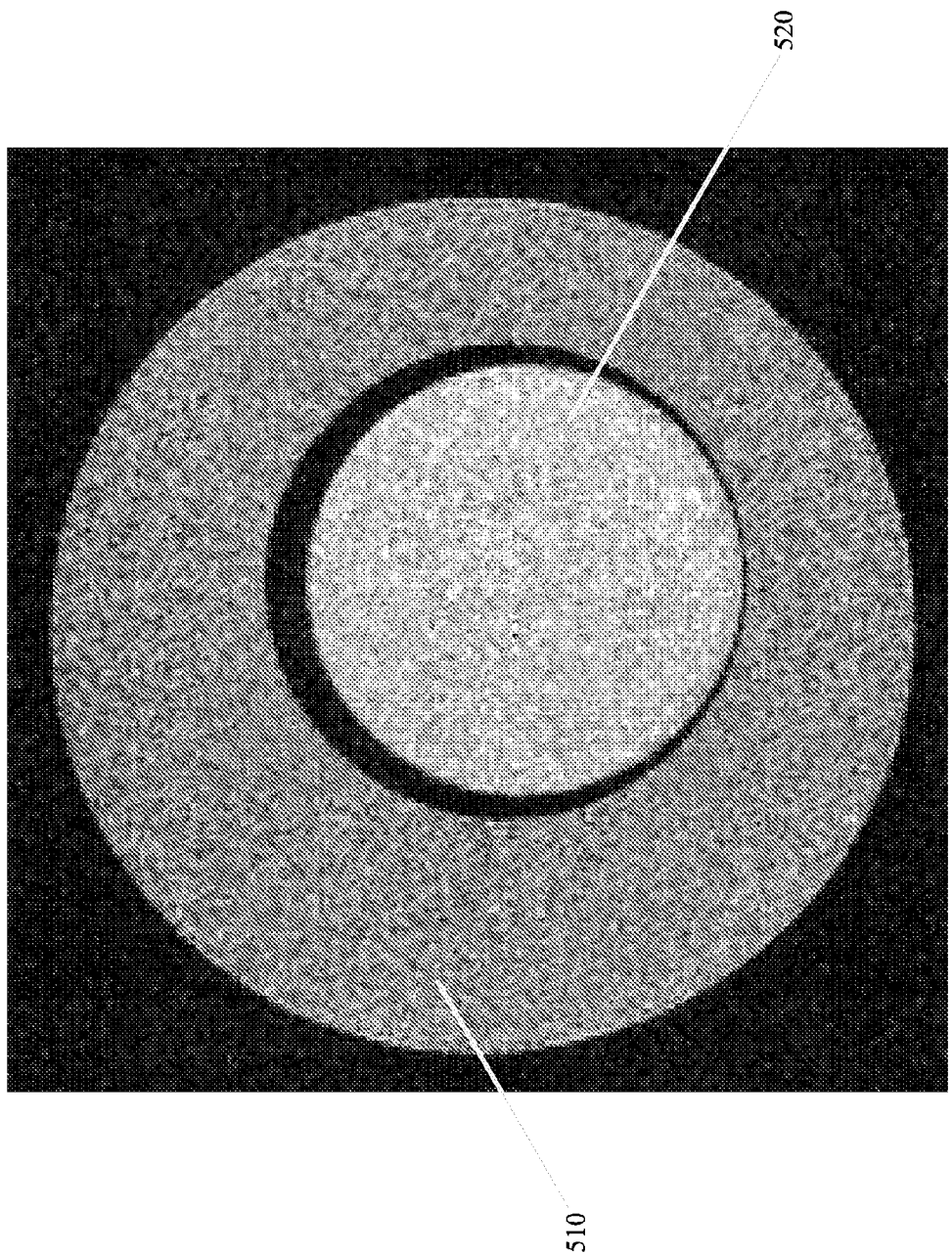
FIG. 5 shows a gradient recalled echo (GRE) image of the phantom used in the first set of experiments described herein, indicating lactate and polyunsaturated fatty acid (PUFA).

All Sel-ZQC experiments described herein were performed on a horizontal bore Varian 9.4T MR spectrometer for small animal imaging and spectroscopy. In a first set of experiments, a two-compartment phantom containing pure vegetable oil in the inner 10 mm nuclear magnetic resonance (NMR) tube and 100 mM lactate in saline solution in an outer 20 mm NMR tube was used for 2-dimensional (2D) Sel-ZQC spectral acquisition of the lactate signal (although other chemicals could be used additionally or alternatively), demonstrating the feasibility of the Sel-ZQC spectroscopic imaging techniques described herein. As explained herein, 2D-SelZQC data may be obtained with spatial localization, such as via the inclusion of phase and frequency gradients, or alternatively via a set of 2D- or 3D-gradients for fast k-space mapping, such as fast MRSI techniques, e.g., fast spiral or echoplanar techniques. The magnetic field was de-shimmed to produce a broadened water peak of 280 Hz line-width. FIG. 5 shows a gradient recalled echo (GRE) image of the phantom used in the first set of experiments described herein, indicating lactate in saline solution at 510 and polyunsaturated fatty acid (PUFA) at 520.

Figure 6:
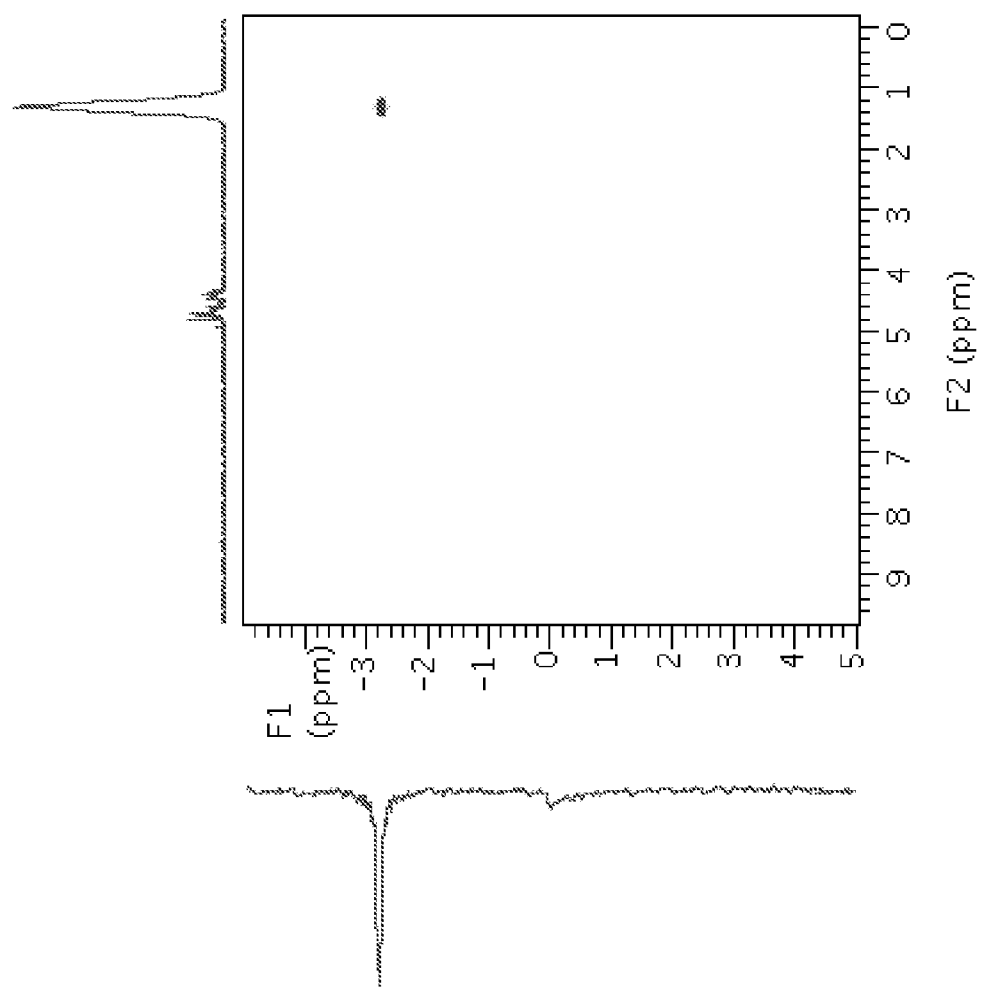
FIG. 6 illustrates a 2D Sel-ZQC spectrum of lactate with complete lipid and water suppression.
Figure 7:
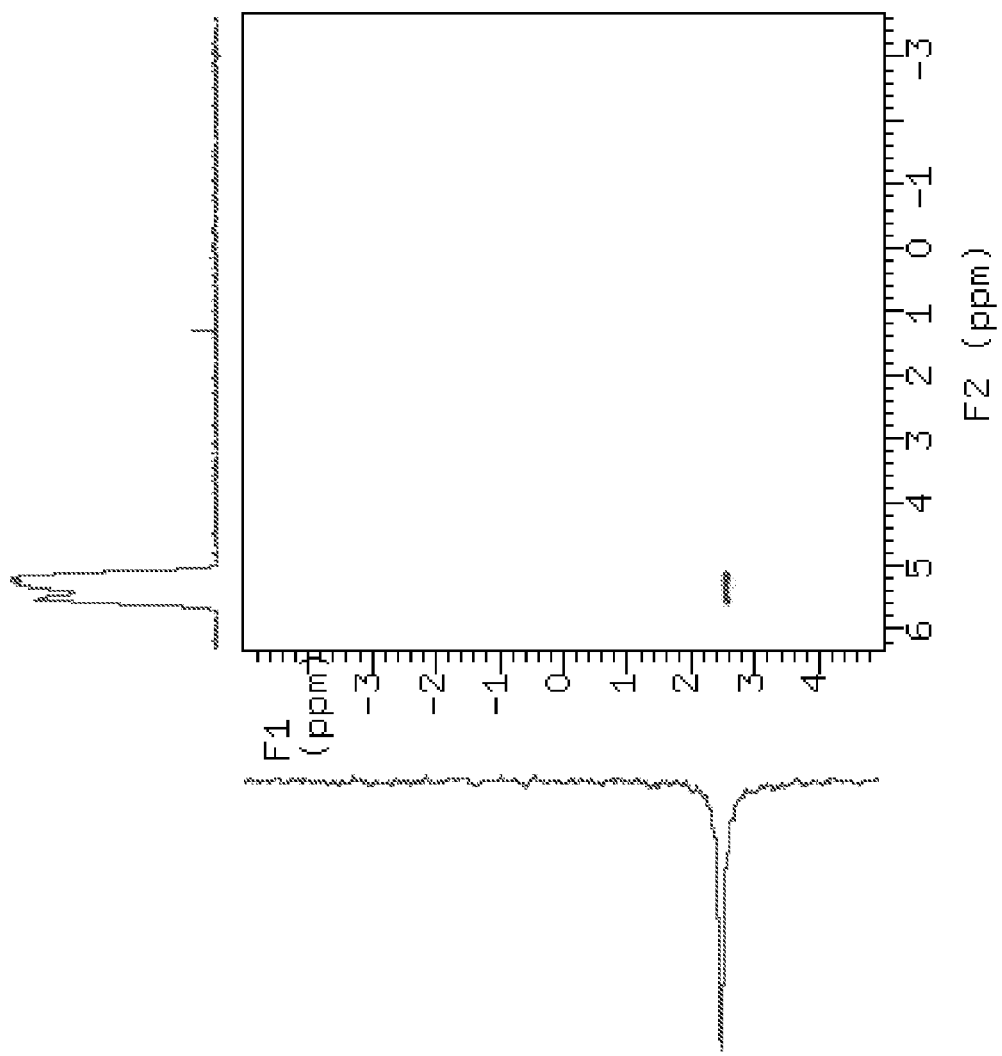
FIG. 7 illustrates the 2D Sel-ZQC spectrum of PUFA acquired from vegetable oil.

In the 2D Sel-ZQC spectra, a ZQ cross peak of lactate ($F_1$, $F_2$)=(−2.8 ppm, 1.3 ppm) was detected at the difference frequency of lactate $CH_3$ and CH proton chemical shifts at 1.3 and 4.1 ppm, respectively. The strong water and lipid signals were completely suppressed by the DQF gradients. FIG. 6 illustrates a 2D Sel-ZQC spectrum of lactate with complete lipid and water suppression. As seen in FIG. 6, the projected 1D ZQ lactate spectrum in the $F_1$ dimension (on the left of the graph) showed a sharp narrow peak without being affected by inhomogeneous broadening, although it had a broadened lactate peak of 280 Hz line-width in the $F_2$ dimension (on the top of the graph). The intermolecular multiple-quantum coherences (iMQCs) were reduced by applying the gradients in the magic angle direction ($\cos^{-1}(1/\sqrt{3})\approx54.74°$ relative to the $B_0$ direction). Polyunsaturated fatty acid (PUFA) was also selectively detected from vegetable oil in a 20 mm NMR tube. FIG. 7 illustrates the 2D Sel-ZQC spectrum of PUFA acquired from vegetable oil at ($F_1$, $F_2$)=(2.5 ppm, 5.3 ppm). Again, as with FIG. 6, the projected 1D ZQ PUFA spectrum of FIG. 7 in the $F_1$ dimension (on the left of the graph) showed a sharp narrow peak without being affected by inhomogeneous broadening, although it had a broadened peak in the $F_2$ dimension (on the top of the graph).

The first set of experiments, discussed above, demonstrated the capabilities of the Sel-ZQC techniques associated with systems and methods of the subject innovation. As is clear from the foregoing, Sel-ZQC is an effective method to study metabolism in vivo in extracranial organs or brain tumors that contain high fat content, including breast cancer, at ultrahigh magnetic field without being subjected to $B_0$ field inhomogeneity and magnetic susceptibility signal distortions.

The foregoing has described selective zero-quantum coherence transfer (Sel-ZQC) systems and methods for ultrahigh field imaging of metabolites and biochemical in vivo without magnetic susceptibility artifacts and $B_o$ inhomogeneous line broadening. However, indirect detection of ZQCs in the ZQ-dimension can be time consuming to generate ZQ-spectra of metabolites for clinical MRSI applications, due to the relatively long sampling time required. However, in aspects of the subject innovation, Sel-ZQC can be modified using techniques described herein, such as via compressive sampling (or compressed sensing) in the ZQ-dimension of Sel-ZQC to reduce approximately 70% data points without degrading image quality.

Compressed sensing (or compressive sampling, etc.; the technique is known by multiple names) is a technique that can be used to find sparse solutions to underdetermined linear systems. The technique can be employed in various settings to reconstruct a signal from less information than otherwise required by the Nyquist-Shannon sampling theorem, such as where signals are either sparse (e.g., where the Fourier transform consists of a relatively small number of discrete frequencies) or compressible (e.g., where the Fourier transform is dominated by a relatively small number of discrete frequencies, with other coefficients being below a threshold), and can recover an exact or nearly exact solution at a significantly lower sampling rate than would otherwise be required, if the under-sampling is random.

In the compressed sensing (CS)-SelZQC method, the modified Sel-ZQC pulse sequence of FIG. 4 can be used to acquire high-resolution Sel-ZQC images with random under-sampling schemes in the ZQ-dimension to ensure incoherence required by the CS theory.

To demonstrate the principle, a second set of experiments were conducted, using the Sel-ZQC edited signal of polyunsaturated fatty acids (PUFA) from a phantom of vegetable oil in a 50 mL conical tube. As with the first set of experiments, the second set were also performed on a horizontal bore Varian 9.4T MRI spectrometer for small animal imaging and spectroscopy. The magnetic field was de-shimmed to produce a broadened line shape of 400 Hz line width in the first single-quantum (SQ) dimension.

In the CS-SelZQC experiments, the PUFA olefinic methylene protons (indicated in bold: —CH═CH—) at 5.4 ppm were selectively excited by the first selective Gaussian 90° pulse (in the excitation band I). The second selective 90° pulse excited the PUFA allylic methylene protons (indicated in bold: ═CH—CH$_2$—CH═) at 2.8 ppm and other lipid signals in the excitation band S at the end of the MQ-preparation period at $\tau=1/2J$ and converted the PUFA antiphase magnetization into the MQ-modes, where J was the scalar coupling constant between olefinic and allylic methylene protons of PUFA. In the subsequent ZQ-evolution period, $t_1$, zero-quantum coherences of PUFA were selected by the ZQ-gradient, $g_{ZQ}$. The selective 180° pulse at 5.4 ppm on PUFA —CH═CH— protons (indicated in bold) converted the selected ZQC of PUFA into the DQ mode, and the last selective 90° pulse on ═CH—CH$_2$—CH═ protons (indicated in bold) at 2.8 ppm converted the PUFA DQ coherence into the single-quantum (SQ) magnetization for detection. Unwanted signals from lipid (and tissue water) were suppressed by a pair of double quantum filter (DQF) gradients ($g_1:g_2=-1:2$). A frequency-encoding and a phase-encoding gradient were applied to image the edited PUFA signals.

Figure 8:
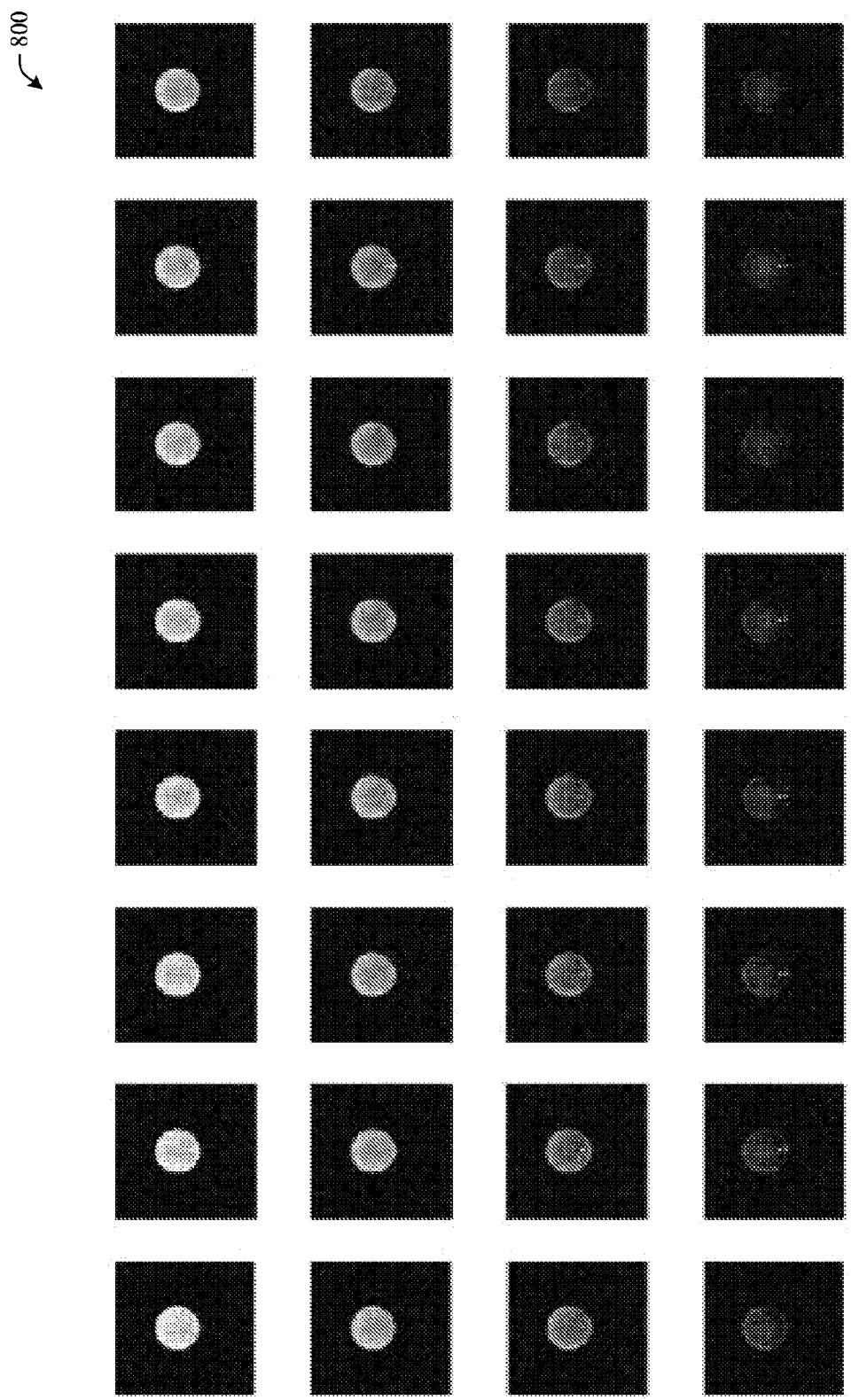
FIG. 8 illustrates 32 images taken during compressed sensing Sel-ZQC experiments discussed herein.
Figure 9:
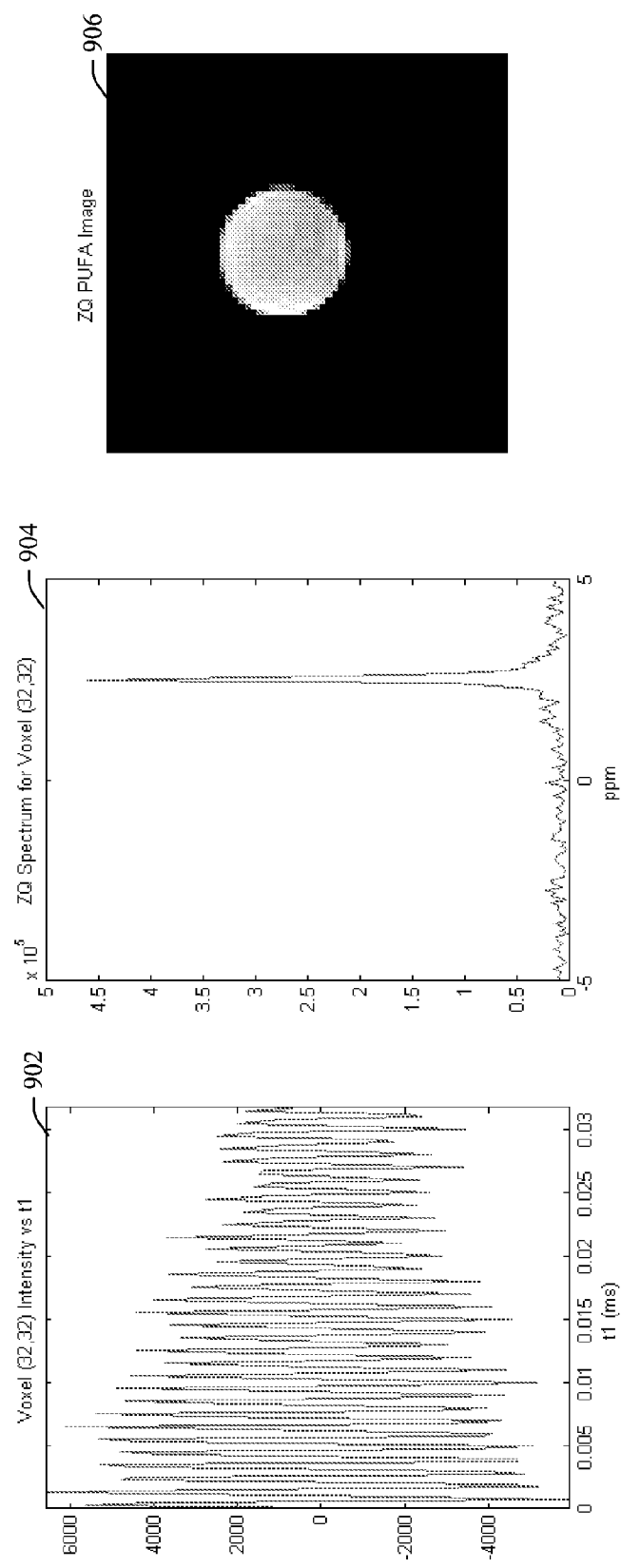
FIG. 9 shows data obtained from the Sel-ZQC images of FIG. 8.

FIG. 8 illustrates 32 images of the 128 images (every fourth image) taken for the CS-SelZQC experiments. The series of 128 Sel-ZQC images was acquired by incrementing $t_1$ by 1/4000 Hz on a 9.4T Varian horizontal bore MRI spectrometer. The resolution was 64×64×1, with a field of view (FOV) of 60 mm×60 mm×10 mm, TR of 1 s, and $SW_{ZQ}$ (where $SW_{ZQ}$ is the spectral width in ZQ-dimension) of 4000 Hz. FIG. 9 shows data obtained from the Sel-ZQC images of FIG. 8. Using the above-described Sel-ZQC sampling scheme, the constant time increment $\Delta t_1=1/SW_{ZQ}$ was applied to obtain a reference ZQ data array in the time domain, as shown at 902, a plot of the signal intensity as a function of ZQ-evolution time $t_1$ of the (32, 32) voxel of the 64×64 voxel array in the PUFA images of Sel-ZQC. The corresponding ZQ-spectrum in frequency domain after fast Fourier transform (FFT) for voxel (32, 32) is shown at 904, and 906 shows a PUFA spectroscopic image created by integrating the ZQ peak area of PUFA for all imaging voxels voxel-by-voxel.

Subsequently, the raw time domain data was randomly under-sampled in the ZQ-dimension—i.e., only a subset of the acquired data of random time points was kept to ensure incoherence. For each selected time point in ZQ-dimension, a 2D Fourier transform (FT) was performed on the corresponding k-space data acquired in the two orthogonal imaging dimensions. Finally, the full 3D frequency domain data was obtained by formulating the reconstruction problem as one that recovers sparse signals by convex programming using compressive sampling techniques (implemented via the L1-magic package).

In a related portion of the second set of experiments, a 2D Sel-ZQC spectroscopy experiment was performed without applying the frequency-encoding and phase-encoding gradients. These experiments developed upon results obtained above.

Figure 10:
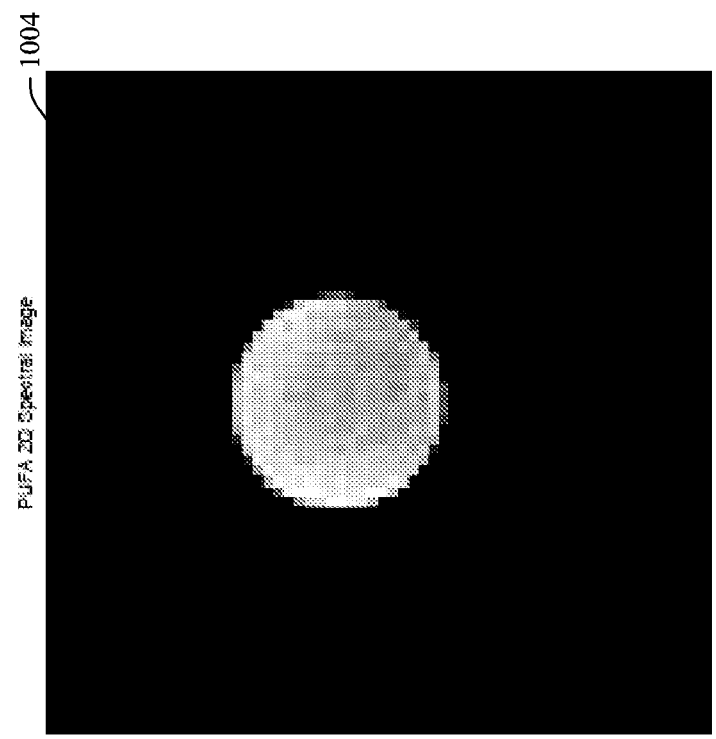
FIG. 10 illustrates the ZQ-spectra for a representative voxel of the PUFA sample and the PUFA image obtained by CS after 50% sampling point reduction.
Figure 10:
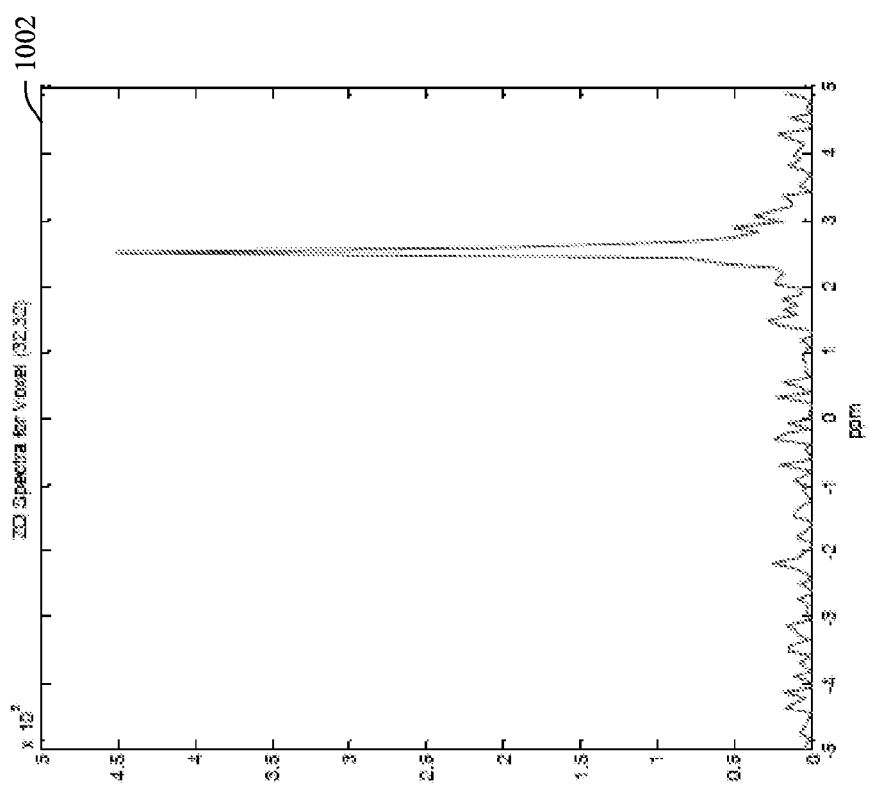
Figure 11:
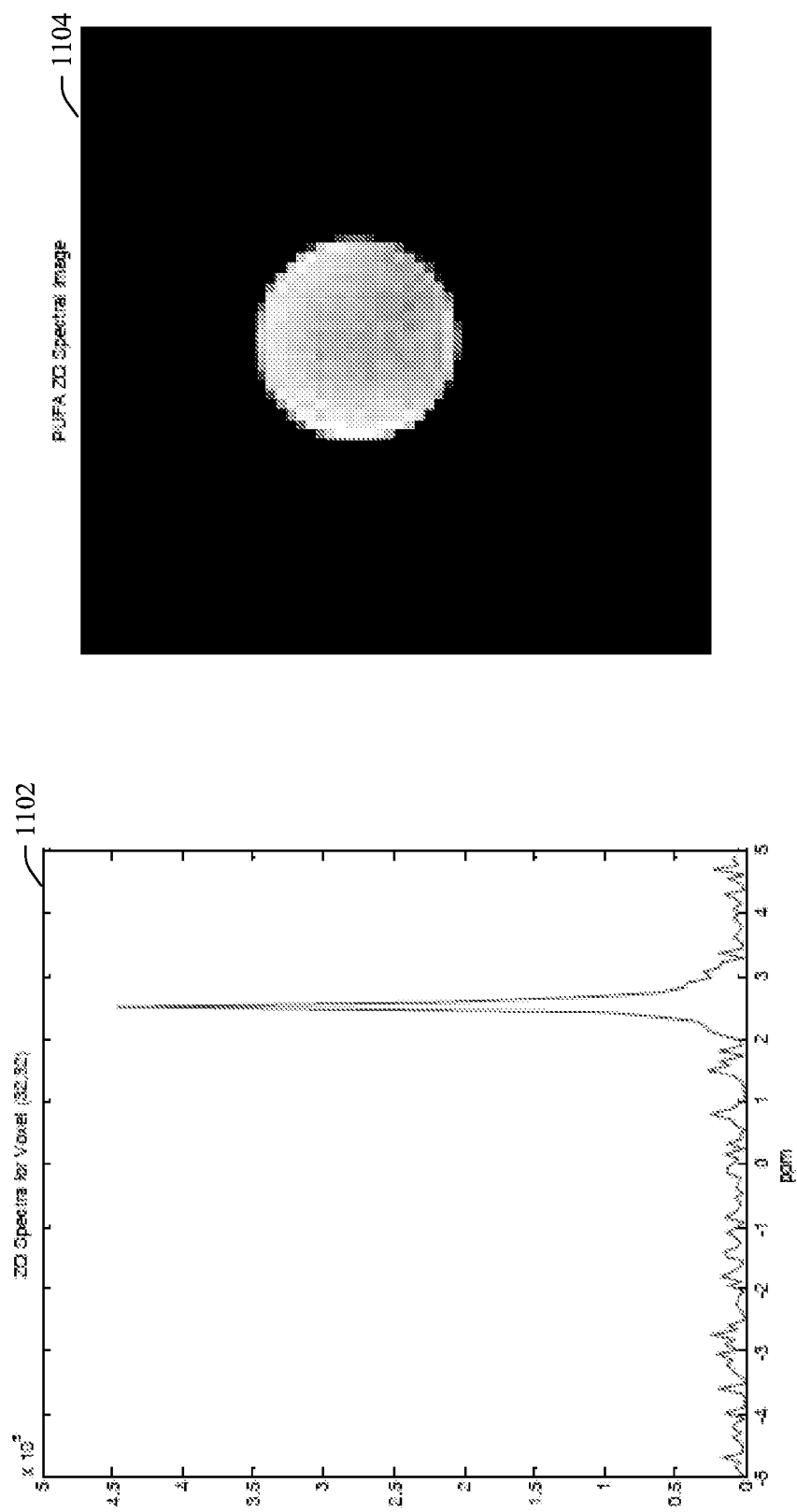
FIG. 11 illustrates the ZQ-spectra for the representative voxel of the PUFA sample and the PUFA image obtained by CS after 70% sampling point reduction.

Compressive sampling was applied to randomly selected (in the ZQ-dimension) subsets of the data points to demonstrate the effectiveness of the technique in connection with systems and methods of the subject innovation employing Sel-ZQC. Data points in the ZQ-dimension were selected via random sampling schemes to ensure incoherence did not deteriorate the PUFA images. FIG. 10 illustrates the ZQ-spectra for a representative voxel (32, 32) at 1002, and the PUFA image at 1004, obtained by CS after 50% sampling point reduction. FIG. 11 illustrates the ZQ-spectra for the same voxel (32, 32) at 1202, and the corresponding PUFA image at 1104, obtained after 70% sampling point reduction. The 30% selected time point numbers from the 128 acquired data (128*0.3=38 points) were: 5, 9, 10, 13, 15, 24, 25, 35, 36, 38, 40, 45, 47, 48, 50, 54, 63, 64, 65, 69, 77, 79, 80, 82, 87, 89, 101, 102, 104, 105, 109, 113, 117, 120, 122, 125, 126, and 128.

As shown by the second set of experiments, compressed sensing in Sel-ZQC can effectively reduce data acquisition time in the ZQ-dimension with little or no degradation in signal-to-noise ratio (SNR) or spatial resolution of the PUFA images. In accordance with aspects of the subject innovation, the CS-SelZQC approach can suppress non-target lipid and water signals in a single scan with potential applications in metabolic imaging of human breast cancer or other diseases in extracranial organs or brain tumors with high fat content at ultrahigh or low magnetic field.

The following discussion includes further aspects of the subject innovation, explanation of systems, methods, and techniques useable in connection with the subject innovation, as well as more detailed explanation of related concepts.

Figure 12:
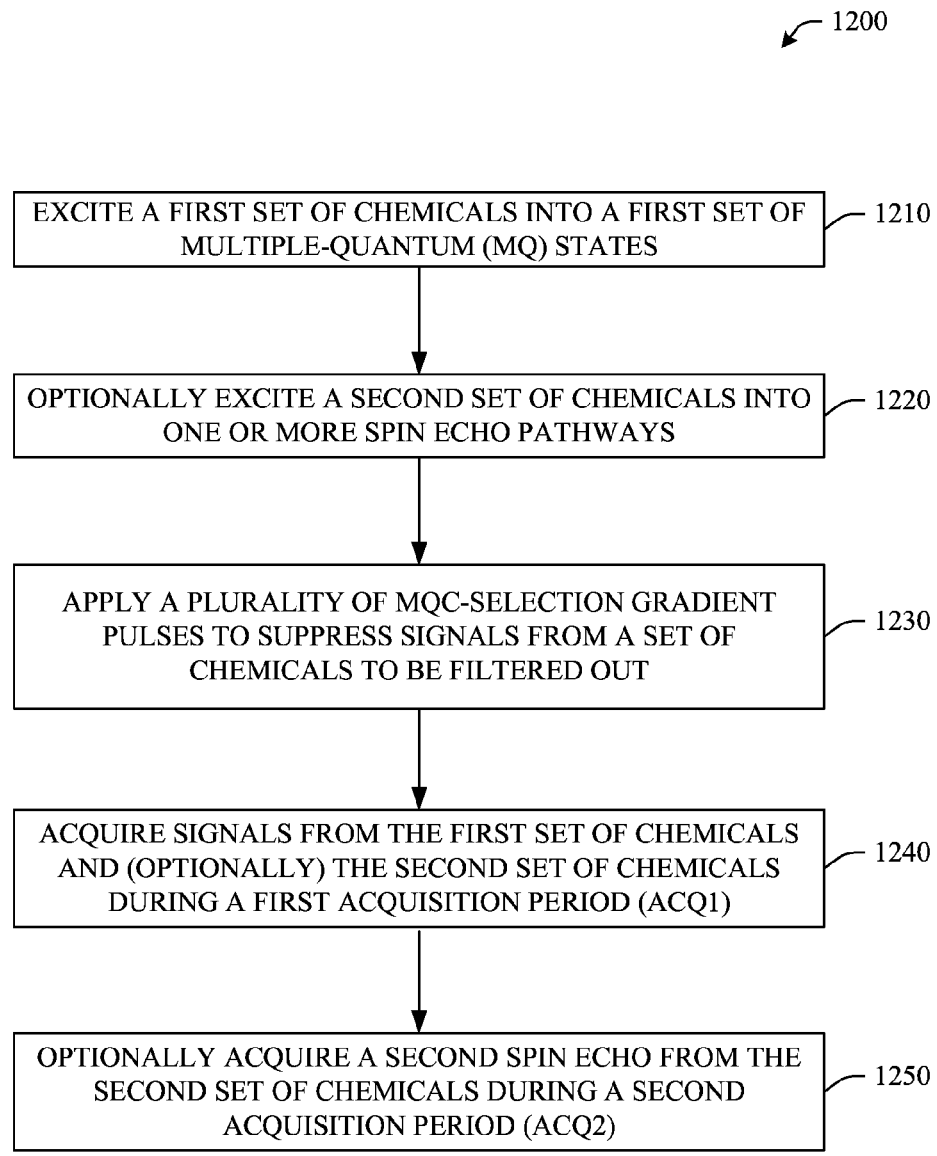
FIG. 12 illustrates an example flowchart of a methodology for selectively obtaining magnetic resonance signals from a first set of chemicals while suppressing non-target chemicals via a multiple quantum coherence (MQC) technique.

FIG. 12 illustrates an example flowchart 1200 of a methodology for selectively obtaining magnetic resonance signals from a first set of chemicals while suppressing non-target chemicals via an MQC technique. In various aspects, one or more techniques can be employed in conjunction (e.g., a ZQC technique such as Sel-ZQC, CS-SelZQC, etc.; an MQC technique such as Sel-MQC; spin echo techniques; etc.). At step 1210, the first set of chemicals can be excited into a first set of multiple-quantum (MQ) states. This can prepare the first set of chemicals for simultaneous detection during a single scan. When the first set of chemicals includes more than one chemical, the first set of MQ states can be different states, and the first set of chemicals can be excited into the different MQ states via different coherence transfer pathways. The first set of chemicals can include, for example, one or more of lactate, a polyunsaturated fatty acid (PUFA), etc. However, chemicals which cannot undergo multiple quantum coherence transitions (e.g., choline) cannot be in the first set of chemicals. Optionally, at step 1220, a second set of chemicals can be excited into one or more spin echo pathways or other independent pathways. Signals from chemicals which cannot undergo MQC transitions (e.g., choline) can be recovered by exciting them into spin echo pathways or other pathways for later signal acquisition.

At step 1230, a plurality of MQC-selection gradient pulses can be applied to suppress signals from a set of chemicals to be filtered out. The plurality of gradient pulses can be designed to selectively remove signals for the set of chemicals to be filtered out. These gradient pulses can be designed based on known information about the first set of chemicals, the second set of chemicals (if they are to be measured), and the set of chemicals to be filtered out (alternatively referred to as "non-target" chemicals, compounds, molecules, signals, etc., or referred to as chemicals, compounds, molecules, signals, etc. to be removed). These differences can be based on differences in chemical shift between the compounds when exposed to an external magnetic field $B_o$, and can be determined based on known characteristics of the molecular topologies involved. In an example embodiment discussed further herein, the plurality of gradient pulses can comprise five gradient pulses $g_1$ through $g_5$ such that $g_1:g_2:g_3:g_4:g_5=-5.25:-3:5.25:-7.5:-6$, with an optional pair of crusher gradients $g_6$ as discussed further herein, with amplitude of −8.

Turning to step 1240, signals from the first set of chemicals and (optionally) the second set of chemicals can be acquired during a first acquisition period ACQ1. Optionally, at step 1250, a second spin echo can be acquired from the second set of chemicals during a second acquisition period. In order to acquire the second spin echo, a selective pulse can be used at a resonant frequency of the second set of chemicals, along with a pair of crusher gradients, which can be employed to reduce other signals.

The spin editing techniques discussed herein can be used to selectively remove signals from non-target chemicals while acquiring signals of interest. Spin network information based on the molecular topology of chemicals can be used to design pulses and pulse sequences to selectively excite the first or second set of chemicals into desired pathways, such as ZQC, MQC or spin echo pathways. Depending on the chemicals to be detected (e.g., the chemicals in the first and optional second set of chemicals), different chemicals may need to be suppressed. For example, drug concentrations in vivo are typically low, and may require suppression of metabolites (e.g., lactates, lipids). The known molecular structure(s) of non-target chemicals to be suppressed can be used to select and design parameters for sequences such as those described herein in order to suppress the non-target chemicals and obtain signals of the first and optional second set of chemicals without signals from the non-target molecules.

In embodiments, the systems and methods of the subject innovation can be used to selectively obtain magnetic resonance data corresponding to a small number of target chemicals (e.g., the first and optional second sets of chemicals), while blocking signals from other chemicals. For in vivo applications, particularly in extracranial applications, lipid and water concentrations are high, and without signal editing such as described herein, can effectively prohibit acquisition of other signals of interest. However, using systems and methods of the subject innovation, particular molecular structures of relatively low concentration can be detected from among a collection of chemicals that include non-target chemicals of higher concentrations.

Figure 13:
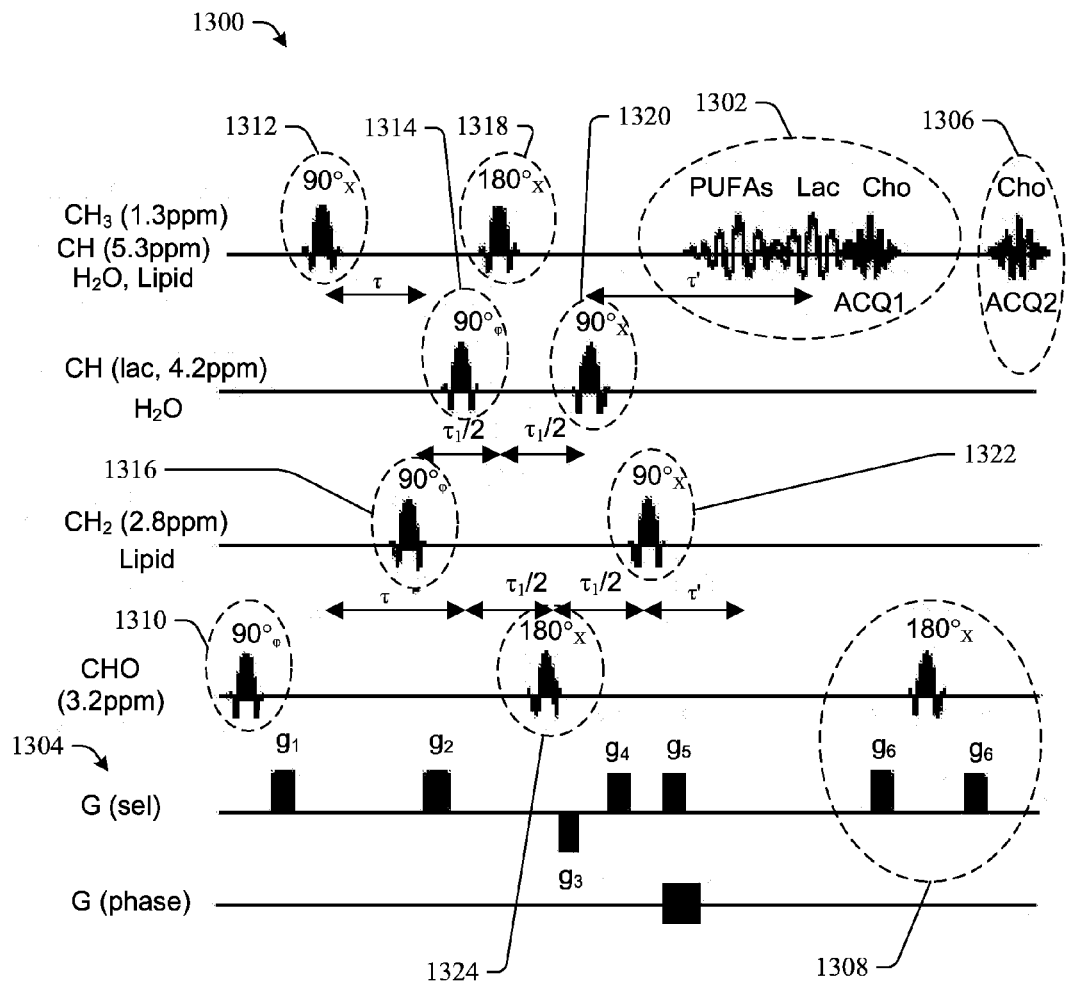
FIG. 13 illustrates an example molecular specific coherence (MSC-SelMQC) sequence that can be employed in connection with aspects of the innovation.

With continued reference to the drawings, FIG. 13 illustrates an example MSC-SelMQC sequence 1300 that can be employed in connection with aspects of the innovation. The example MSC-SelMQC CSI sequence shown in FIG. 13 is modified from the Sel-MQC CSI pulse sequence, and can provide for simultaneous mapping of multiple molecules of interest, including a first set of chemicals (e.g., PUFA, lactate, etc.) and a second set of chemicals (e.g., choline). This example sequence illustrates some of the approaches discussed in connection with FIG. 12 and the associated concepts. For example, some molecules, such as choline, do not go through MQC transitions and cannot be put into MQ or ZQ modes, but choline signals can be obtained using spin-echo techniques. By varying parameters associated with example sequences discussed herein, different molecular structures can be detected, allowing for acquisition of data from chemicals different than in the examples provided herein, and the same or other non-target chemicals can be suppressed. The example sequence 1300 can excite lactate and PUFA (which can be in the first set of chemicals) into different multiple-quantum (MQ)-states via two different MQ coherence transfer pathways, and choline (which can be in the second set of chemicals) into the spin echo pathway for simultaneous detection in the first acquisition period (ACQ1) as shown at item 1302, leaving non-target lipid signals and water (which can be in the set of chemicals to be filtered out) in the SQ modes to be completely suppressed by the MQC-selection gradient pulses g1 through g5 shown on line 1304, which, in the example sequence shown, are in the combination g1:g2:g3:g4:g5=−5.25:−3:5.25:−7.5:−6.

A second choline echo 1306 can be obtained using a selective 180° pulse at 3.2 ppm and a pair of crusher gradients with amplitude g6=−8, as shown at item 1308. The choline magnetization can be excited by a first 90° choline selective pulse 1310 and labeled by gradient g1 of line 1304. A cosine modulated 1-lobe 90° sinc pulse (e.g., of 10 ms duration) 1312 can be applied to excite the olefinic methylene protons of PUFA at 5.3 ppm and the lactate methyl $CH_3$ protons at 1.3 ppm. The excited lactate and PUFA protons can then evolve into anti-phase magnetization via J-coupling in the preparation period of $\tau=1/(2J)$, where J is the scalar coupling constant of lactate or PUFA coupled spins.

A third 90° pulse 1314 can be applied at the lactate CH resonant frequency (4.2 ppm) to generate lactate MQ coherence, which can be refocused by the coherence labeling gradient g3:(g4+g5−g2)=1:−2 (as shown on line 1304) in the ZQ (zero quantum)→DQ (double quantum) coherence transfer pathway, whereas a gradient g2 as shown on line 1304 can serve as a Te-crusher. A fourth 90° selective pulse 1316 can excite the allylic methylene protons of PUFA at 2.8 ppm to generate PUFA MQC. The PUFA MQC echo can be refocused (g2:g5=1:2) via the DQ→ZQ coherence transfer pathway, where g3+g4=2.28 can serve as a $T_1$-crusher. A cosine modulated sinc 180° 1318 (e.g., of 10 ms duration) can be applied at the lactate $CH_3$ 1.3 ppm and PUFA at 5.3 ppm to inter-convert the DQ and ZQ conference transfer pathways for both lactate and PUFA. The multiple quantum coherences of both PUFA and lactate can be converted into single-quantum (SQ) states respectively by a last lactate CH 90° sinc pulse 1320 at 4.2 ppm and a last PUFA $CH_2$ 90° pulse 1322 at 2.8 ppm for detection in the first acquisition window (ACQ1), as shown at 1302. Optionally, choline signals can be refocused twice at 1324 and 1308 for both a first and second echo acquisition in window ACQ1 at 1302 and ACQ2 at 1306, respectively. Additionally or alternatively, chemicals placed in the ZQ mode can be recovered indirectly as described above in connection with Sel-ZQC and CS-SelZQC techniques when DQ-evolution period is fixed as a constant time delay. This can be especially useful in situations where magnetic field inhomogeneities or susceptibility effects would otherwise affect signal clarity.

The sequences provided herein (e.g., in connection with FIGS. 3, 4, and 13) can be modified to obtain signals from other chemicals than those discussed therein, to suppress signals from other chemicals than those discussed therein, or both. However, the principles are the same as those set forth above. The parameters listed above (e.g., resonance frequencies, timing of pulses) will vary based upon changes in chemicals. The spin coupling network of one or more known molecules can be analyzed to determine one or more resonance frequencies. The pulse sequences described herein can be modified by setting pulses to different resonant frequencies corresponding to the one or more known molecules. Activation frequency offsets of radio frequency (RF) pulses can be changed in order to pick up the one or more known molecules, based at least in part on one or more scalar coupling constants associated with the one or more known molecules. By applying one or more RF pulses at resonance frequency of the one or more known molecules as described herein (e.g., corresponding to two spins coupled to one another), the spin from only the one or more known molecules can be selected and excited into one or more particular pathways (e.g., a ZQC or MQC transfer pathway or a spin echo pathway). By applying filtering techniques described herein, signals from non-target molecules in SQ states can be suppressed, and the signals of the one or more known molecules of interest can be recovered in 1D- or 2D-MRS spectra for all voxels.

In aspects, the innovation can provide for the simultaneous detection of multiple chemicals of interest (e.g., PUFA, lactate and choline) using MSC-SelZQC method with complete suppression of selected signals to be removed or filtered out (e.g., non-target lipid and water signals). The systems and methods discussed herein can be applied to study animal tumor models and human cancer (e.g., breast or other cancers, extracranial or cranial) in tissues containing a high concentration of fat. Additionally, the innovation can be applied in other contexts, for example, detection or monitoring of diseases with known chemical markers, research to determine whether specific chemical markers are associated with certain diseases, or monitoring the effectiveness of treatment (e.g., radiotherapy, chemotherapy, etc.). These systems and methods can be employed in vivo on both intracranial and extracranial tissue. In the latter case, these systems and methods are superior to traditional MRSI techniques, which produce poor results due to the magnetic susceptibility artifacts, $B_0$ broadening, and relatively high concentrations and corresponding signal strengths of lipids and water in extracranial tissue.

Aspects of the innovation relate to improvements in magnetic resonance spectroscopic imaging (MRSI), which is a type of imaging based upon nuclear magnetic resonance (NMR). All atomic nuclei are composed of one or more protons and zero or more neutrons, and the total number of nucleons (protons or neutrons) of an isotope of an element can be written as a superscript number before the chemical symbol of the element, such as $^1H$ (one proton and no neutrons) or $^{13}C$ (six protons and seven neutrons).

All protons and neutrons have an intrinsic angular momentum known as spin that can interact with a magnetic field. Nuclei that have an odd number of protons or neutrons can have a net spin other than zero, and as a result, the nucleus can also have a non-zero magnetic moment, $\mu=\gamma S$, where $\mu$ is the magnetic moment, S is the total spin of the nucleus, and $\gamma$ is the gyromagnetic ratio, which depends upon the g-factor of the nucleus in question and the nuclear magneton. Because of the magnetic moment of the nucleus, different nuclear spin levels will correspond to different energy levels when the nucleus is exposed to an external magnetic field. The energy levels of a magnetic moment in a magnetic field are proportional to the amplitude of the magnetic field and to the magnetic moment. The transitions between these energy levels can be detected through MRI, MRS, or MRSI.

In an external magnetic field, the magnetic moment of a nucleus will undergo Larmor precession, processing around the direction of the magnetic field with a frequency called the Larmor frequency which is proportional to the gyromagnetic ratio and the amplitude of the field. Because of the variations in gyromagnetic ratios, the Larmor frequency also varies for different isotopes. As used herein, "$B_0$" refers to an external (frequently relatively uniform and constant, although non-uniform and/or non-constant fields are contemplated within the scope of the subject innovation and can be used in connection with techniques described herein, especially those based on Sel-ZQC) magnetic field primarily responsible for the separation of energy levels. Changes can be induced or measured by altering the magnetic field, such as by applying one or more other magnetic fields, $B_1$ (frequently perpendicular to or having a component perpendicular to $B_0$), for example, one or more fields oscillating at or near the Larmor frequency of a nucleus or nuclei of interest.

One potential application for the systems and methods discussed herein is improved detection of cancer in vivo, as well as monitoring the effectiveness of treatment. Malignant tumors frequently have multiple common tumor-specific markers that systems and methods of the subject innovation can detect to facilitate cancer diagnostics. Magnetic resonance spectroscopy can be sensitive to tumor physiology and biochemistry. Human cancer has specific metabolic characteristics that may be exploited to obtain useful diagnostic and prognostic information. $^1H$ MRS improves the detection sensitivity of metabolites by employing protons, the most abundant and sensitive nuclei in metabolites or drugs. However, traditional proton MRS needs more sophisticated techniques for water and lipid suppression, such as those discussed herein, because the tissue proton spectra of most extracranial organs usually are dominated by intense water and lipid resonances that block observation of metabolites and drugs by traditional MRS. Breast tissue represents the worst case scenario for the $^1$H MRS observation of metabolites and drugs, due to the elevated lipid levels. However, systems and methods of the subject innovation, via suppression of water and lipid signals, can recover signals of metabolites, drugs, etc. from such tissue. Additionally, although traditional MRS has had more success with imaging of the brain, brain tumors can be associated with elevated lipid levels that can interfere with the imaging of metabolites or drugs, unless systems and methods such as those described herein are employed.

The particular metabolic characteristics of tumors can cause several distinguishing chemical markers to be present in them, because neoplastic cells that develop into tumors activate specific metabolic pathways to develop into 3D spheroids and solid tumors. Microregions of heterogeneous cell environments are associated with the development of abnormal vascularization in malignant tumors, which often consist of distended capillaries with leaky walls and sluggish flow, as compared with the regular, ordered vasculature of normal tissues. Despite the constant effort of tumor cells to recruit new blood vessels, there are significant gradients of critical factors for cell growth, such as oxygen, glucose, other nutrients, and growth factors. Hypoxia occurs in tumor cells that are 100-150 µm away from the nearest blood vessel and tends to be widespread in solid tumors observed as multifoci (or "multiforme"). The anaerobic metabolism of glucose provides a major energy source for tumor cells in hypoxic regions. For example, hypoxia also contributes to processes that directly favor malignant cell progression through effects on the expression and activity of mutated tumor suppressor proteins such as p53 and oncogenes. It appears that hypoxia can act as a selective physiological pressure against the survival of wild-type p53 cells in a tumor, thus favoring oncogenesis through enrichment of the population of mutant p53 cells.

A striking common feature of tumor cells is the production of high levels of lactic acid. The last enzyme of glycolysis, lactate dehydrogenase A (LDH-A) is an epidermal growth factor, cAMP, and phorbol ester-inducible protein that has been a widespread prognostic tumor marker. The elevated LDH-A levels will result in increased production of lactic acid within tumor cells.

Systems and methods discussed herein can observe proton signals of metabolites, antineoplastic agents, and unsaturated lipids in tissues with high concentrations of mobile fat. Lactate can be an index of radiation treatment and early chemotherapeutic responses. For example, radiosensitive tumors show a significant decrease in lactate levels at 48 hours after treatment when compared with radioresistant tumors. As an example related to chemotherapy, the lactate levels in RIF-1 tumors has been found to decrease following therapeutic intervention with cyclophosphamide (Cp, 300 mg/kg), which correlates with the increases in tumor perfusion and permeability characterized by the Gd-DTPA (Gadolinium diethylenetriaminepentaacetic acid) uptake curves. The decrease in lactate levels may be due to the increased perfusion and tumor re-oxygenation.

Additionally, magnetic resonance systems and methods can be used to monitor drug effectiveness. Proton detection of drugs in vivo, although highly desirable, has not been very successful in the past for two reasons—low tissue drug concentration and overlapping of drug signals with resonances of metabolites, lipids, or water. To circumvent problems with background signals, $^{19}$F NMR has been used to study pharmacokinetics in tissues. This approach, however, often requires chemical modification of the pharmacological agents.

However, with systems and methods such as those discussed herein, the proton MR spectrum of a drug has been observed in vivo. Iproplatin, an antineoplastic agent that cross-links nucleotides in both single and double strand DNA molecules and is used in cancer therapy, can be detected selectively in the RIF-1 murine tumor models. The overlapping lactate methyl proton signals and lipid signals can be removed using techniques described herein. Despite relatively low concentrations of drugs such as Iproplatin in a typical tissue environment as compared with the concentrations of metabolites, lipids and water, it can be detected because of the particular structure of the molecule, which contains twelve protons with each in the same local environment (thus strengthening the corresponding signal by a factor of twelve). Additionally, with editing techniques such as those described herein, other drugs or chemicals in relatively low concentrations could be detected, depending on their structure; $^1$H MRSI systems and methods of the subject innovation are more effective with molecular structures containing a larger number of protons in similar local environments, such as the twelve similar protons of Iproplatin.

In some embodiments, sequences associated with systems and methods described herein can be used to recover signals associated with lactate, or can be modified as described herein to recover signals from metabolites or drugs other than lactate. Sequences associated with these embodiments can be utilized to detect signals from multiple metabolites in a single scan with complete lipid and water suppression. For detection involving a single scan, losses in image quality can be avoided due to motion artifacts.

The in vivo magnetic resonance measurements of lactate level, $^{13}$C-labeled glucose uptake and glycolytic rate, and blood perfusion in tumor tissues of animal tumor models and spontaneous human cancers reflect the physiochemical states of the up-regulation of glucose transporters, glycolytic enzymes, HIF-1 recruited tumor angiogenesis, and tumor cell pH regulation, all of which are related to tumor progression and malignancy. The glycolytic capacity of tumors as measured by lactate production, when normalized for $O_2$ availability, is proportional to the tumor growth rate. High lactate production in fast-growing tumors results from reduced mitochondrial oxidative activity relative to glycolytic capacity to utilize pyruvate. Most rapidly growing tumor cells have the capacity to use much more glucose than their tissue of origin. Additionally, tumors in vivo utilize much more glucose than do tumor cells in culture and produce a large amount of lactic acid. In contrast to cultured cells, cells in solid tumors are exposed to hypoxia, and their mitochondrial oxidative phosphorylation is significantly slowed due to the oxygen requirements of mitochondrial respiratory functions. Three-dimensional tumor growth, therefore, relies on glycolysis.

Rapidly growing malignant tumors have high glycolytic phenotypes due to both the hypoxic tumor microenvironment and genetic changes in the malignant cells. For benign tumors with low growth rates, lactate levels may stay low. Therefore, $^1$H detection of lactate and $^{13}$C measurement of tumor glycolytic rates normalized for tissue oxygen levels may be used to differentiate malignant lesions from benign lesions and normal cells from fibrosis. However, these differentiations may not be able to be resolved by contrast-enhanced MRI and other traditional methods. In contrast, systems and methods in accordance with the subject innovation can suppress selected signals (e.g., water and non-target lipid signals), allowing for improved detection of target chemicals (e.g., lactate, PUFA, choline, antineopastic agents, etc.).

Tumor regions of high permeability often are associated with hypoxia and necrosis and frequently display lower vascular volumes. The difference in tumor microenvironments is coupled with tumor genetic and metabolic changes that can be detected by MRS. For example, a "GPC (glycerophosphocholine) to PC (phosphocholine) switch," which is associated with altered choline phospholipid metabolism in mammary epithelial cells (e.g., increased levels of GPC relative to PC), was observed as an early phenotypic change during tumor progression.

Specifically in reference to breast cancer, breast tissue contains intense lipid and water signals that can present a formidable technical obstacle to the efficient and reliable in vivo proton MRS detection of metabolites as surrogate markers of breast cancer. Traditionally, choline is the only metabolite that has been observed reliably in human breast cancer by single voxel proton MRS. However, choline also has been detected in lactating breast tissue that had a physiologically high metabolism without increase in cell proliferation. Additionally, certain breast cancer types do not have elevated choline. Therefore, choline alone, detected in vivo by $^1$H MRS, may not be a specific marker for breast tissue malignancy. However, in aspects, systems and methods of the subject innovation, can provide for simultaneous detection of choline in connection with other potential markers, such as PUFAs or lactate.

Tumor cells express high levels of fatty acid synthesizing enzymes, use endogenously synthesized fatty acids for membrane biosynthesis, and export large amounts of lipids. Fatty acid molecules can be tumor specific markers. As one example of chemical markers associated with tumors, brain tumors usually present increased choline levels, decreased levels of N-acetyl aspartate (NAA), detectable lactate, and increased lipid concentrations. Aggressive brain tumors in particular produce large amounts of lipids that can interfere with traditional signal acquisition, but which the systems and methods described herein can filter out to perform MRSI for chemicals of interest.

Additionally, in aspects, the subject innovation can be used in conjunction with fast MRSI scanning techniques to speed data acquisition. In connection with MRI, MRS, and MRSI, k-space is a conjugate space to three-dimensional Euclidean space, where the dimensions correspond to conjugate Fourier variables of ordinary spatial variables, and can represent the Fourier transform of a spatial MRI image, etc. As such, images can be obtained by taking Fourier transforms of the corresponding k-space data. Frequently, the center portion of k-space can contain a larger proportion of the information related to signal-to-noise and contrast.

Cartesian k-space mapping of chemicals (e.g., metabolites and PUFA) via CSI in accordance with techniques of the subject innovation can require relatively long acquisition time (for example, at least 10 min for single-scan data acquisition to image a sagittal slice of human breast tissue). However, fast scanning techniques can be used in conjunction with systems and methods described herein to accelerate data acquisition. By way of example, a fast scanning technique called the fast Spiral-SelMQC sequence is described herein. However, other fast scanning techniques may be known by those of skill in the art, and can also be employed in conjunction with the subject innovation.

A fast scanning technique such as a fast Spiral-SelMQC sequence employing a rapid spiral k-space sampling scheme can dramatically reduce the time requirements for data acquisition. In an example experiment, Spiral-SelMQC images of PUFA distribution in human breast were acquired using two-interleaved spirals on a 3T GE Signa MRI scanner. Approximately 160-fold reduction of acquisition time was observed as compared to the corresponding Sel-MQC CSI method with an equivalent number of scans, permitting acquisition of high-resolution PUFA images in minutes. The reconstructed Spiral-SelMQC PUFA images of human breast tissues achieved a sub-millimeter resolution of 0.54× 0.54 or 0.63×0.63 mm$^2$/pixel for FOV (field of view) of 14 or 16 cm, respectively. The Spiral-SelMQC parameters for PUFA detection were optimized in 2D Sel-MQC experiments to suppress monounsaturated fatty acids (MUFA) and other lipid signals. Fast Spiral and other fast MRSI sequences can additionally be employed in connection with other sequences discussed herein, in particular, Sel-ZQC sequences.

Figure 14:
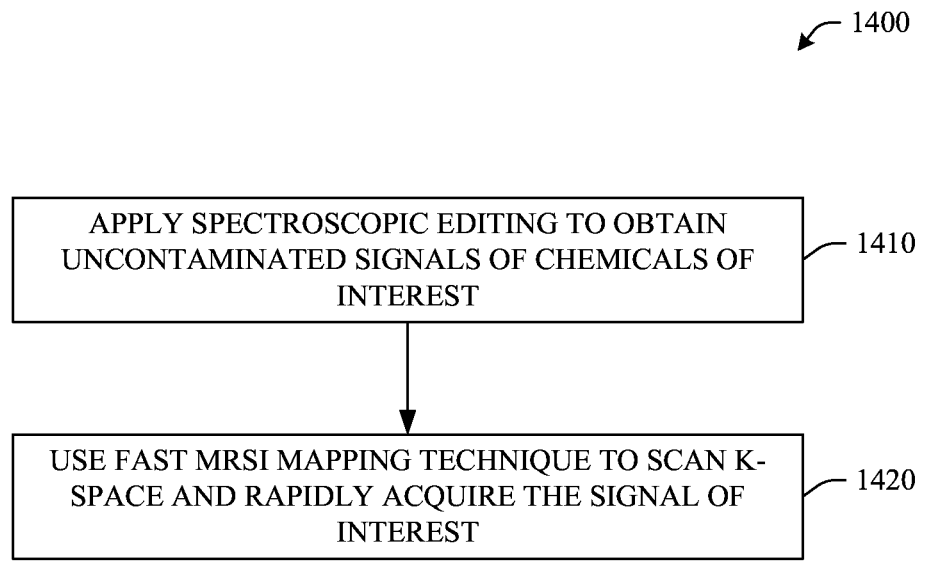
FIG. 14 illustrates a method of employing a fast magnetic resonance spectroscopic imaging (MRSI) technique in connection with aspects of the innovation.

FIG. 14 illustrates a method 1400 of employing a fast MRSI technique in connection with aspects of the innovation. To aid in understanding of aspects of the innovation, fast MRSI techniques are discussed in connection with a specific example provided herein (the Spiral-SelMQC), although other fast MRSI techniques can be utilized instead (e.g., involving Sel-ZQC). The Spiral sequence can modify sequences associated with the systems and methods described herein. It can consist of two steps, as shown in FIG. 14. At step 1410, Sel-MQC spectroscopic editing can be applied to obtain uncontaminated signals of chemicals of interest (e.g., PUFA or Monounsaturated Fatty Acids (MUFA) signals), as described in detail herein, and at step 1420, a fast MRSI technique (e.g., spiral k-space mapping) can be used to scan k-space and to rapidly acquire the signal of interest.

Any of the systems and methods of acquiring signals via sequences that are discussed herein can be employed at step 1410 to obtain the uncontaminated signal. As an additional example of step 1410, the following brief description relates to obtaining a signal of PUFA while removing signals from non-target lipids and water. Accordingly, for illustrative purposes, specific information relating to these chemicals are included, although other chemicals could be used with corresponding changes made. During the preparation time period τ after the slice-selective 90° pulse, the AX$_2$ spin system evolves according to the Hamiltonian containing chemical shift and J-coupling terms, $H=\omega_1 I_{1z}+\omega_2 I_{2z}+2\pi J_{12}I_{1z}I_{2z}$, where $I_{1z}$, $I_{2z}$ are the z-angular momentum and $\omega_1$ and $\omega_2$ are the chemical shifts of spin A and X, respectively, and $J_{12}$ is the spin-spin coupling constant. The two-spin state is produced under the influence of the J-coupling Hamiltonian term to give the spin density matrix, $\rho=I_{1x}\cos(\pi J_{12}\tau)+I_{1y}I_{2z}\sin(\pi J_{12}\tau)$, where $I_{1z}$ and $I_{1y}$ are the x- and y-angular moment of spin A and X, respectively. When $\tau=1/(2J_{12})$, $I_{1x}$ evolves into the anti-phase magnetization $I_{1y}I_{2z}$. The second 90° pulse can create Zero-Quantum (ZQ) coherence, $I_1^+I_2^-$, and Double-Quantum (DQ) coherence, $I_1^+I_2^+$. Higher multiple-quantum coherences (MQC) can also present in lesser quantities. In contrast, magnetizations from water at 4.7 ppm and lipid protons at 1.3 ppm (or, if other chemicals instead of water and lipids are to be filtered out, the corresponding frequencies of those chemicals) can stay in single-quantum (SQ) state, which can be dephased by MQ-selection gradients. The frequency-selective 180° pulse can be applied at 5.4 ppm (or, if the signal of a chemical other than PUFA is to be detected, the corresponding resonance frequency of that chemical) and can interchange ZQ and DQ coherences during the MQ-evolution time delay, $\tau_1$, between the second and the last 90° pulses. The last 90° pulse can convert the ZQ and DQ coherences into an anti-phase single-quantum (SQ) magnetization. In the detection period, the anti-phase magnetization evolves under the J-coupling Hamiltonian term into an in-phase magnetization to form a MQ-coherence transfer echo at $\tau'=1/(2J_{12})-\tau_1$. The remaining magnetization can be dephased by crusher gradients ($G_{crs}$) after data acquisition. A pair of spiral readout gradients ($G_x$, $G_y$) starting at the center of the MQ-coherence transfer echo of PUFA can be applied to achieve rapid 2D k-space mapping in the selected slice. A $T_1$-crusher gradient ($g_1$) and a pair of $t_e$-crusher gradients ($g_{cr}$) can also be applied to spoil the non-target multiple-quantum coherences and transverse magnetization created by imperfect RF pulses.

If the Spiral technique is selected as the fast MRSI technique, the spiral trajectory can be generated in three stages: (a) constant density spiral mapping in the center of k-space followed by (b) variable density spiral mapping in the slew rate limited case, and finally (c) variable density spiral mapping in the amplitude limited case. This sophisticated trajectory reduces spiral imaging and motion artifacts.

In stage (a), the Glover's constant density spiral trajectory, which defines a trajectory $k_c(\tau)=k_{max}\tau e^{iw_k\tau}$, $\tau\in[0,1]$, can be used in the Spiral sequence to sample the k-space center with a constant sampling density, where $k_{max}$ is the radius of the k-space coverage. In this equation, $|k_c(0)|=0$ at the center of k-space when $\tau=0$, and $|k_c(1)|=k_{max}$ when $\tau=1$. Stage (b), the slew rate limited case, can utilize $$\tau(t) = \frac{\frac{1}{2}\beta t^2}{\omega_k\left(\frac{1}{q} + \frac{\beta t^{\frac{4}{3}}}{2\alpha}\right)},$$

where $$\alpha = \left(\frac{9}{4}\frac{s_m}{k_{max}\omega_k^3}\right)^{\frac{1}{3}}, \beta = \frac{s_m\gamma}{k_{max}\omega_k^2},$$

$s_m$ is the maximum slew rate, and $\gamma$ is the gyromagnetic ratio. The constant, q (in one example, q can be 0.2), controls the behavior of $\tau(t)$ when t is small. The gradient waveform g(t) as a function of time can be given by:

$$g(t) = \frac{k'(t)}{\gamma} = \frac{k'(\tau)\cdot\tau'(t)}{\gamma}.$$

As the formula of $k_c(\tau)$ implies, the radial distance $|k_c(\tau)|=k_{max}\tau$ is proportional to the angular distance $\theta=\omega\tau$ so that the distance between neighboring spiral lines is constant. In example Spiral-SelMQC experiments for PUFA imaging, the spiral k-space density was set to 1.3 times the nominal density ($\Delta k'=1.3$ $\Delta k$, $\Delta k=1/FOV$). However, in other situations, other values may be preferable, depending on image acquisition time or resolution requirements. As the trajectories reach a certain point in k-space (for example, approximately 25% of $k_{max}$), the algorithm can switch to a variable density trajectory in k-space given by: $k_v(\tau)=k_{max}f(\tau)e^{i\omega\tau}$, $f(\tau)=a\tau^2+b\tau+c$, where $\tau\in[0,1]$ and a, b, and c can be solved using boundary conditions including the two trajectory switching points. In this way, the k-space center (which, as explained above, frequently provides more information of interest) can be oversampled and the sampling density can gradually decrease toward outer k-space. At the end of the trajectories, the sampling density can be less than the nominal density (in the example above, it was about 0.7 times the nominal density).

As an additional illustrative example, in several experiments, spiral gradient waveforms were generated in real time with a two-shot interleaved spiral implemented to acquire the spectroscopic images of PUFA in breast tissues. The $T_1$ relaxation delay TR was 2s. The total data points per spiral leaf were 2048 for a bandwidth of 125 kHz. The field of view (FOV) in different experiments varied from 12 to 20 cm. The acquired spiral data in k-space was gridded to a corresponding 2D data matrix ranging from 12×12 to 20×20 in size, and then interpolated onto a 256×256 Cartesian matrix. In the re-gridding process, the value at each trajectory point was radially-weighted and transferred to the neighboring points toward the center of k-space on the Cartesian grid. Thus, each Cartesian grid point could accumulate re-gridding values from several neighboring spiral segments. PUFA images were obtained by 2D Fourier transformation of the re-gridded Cartesian Matrix. Reconstructed spiral PUFA images of the human breast had a resolution of 0.54×0.54 or 0.63×0.63 mm²/pixel for FOV=14 or 16 cm.

In these experiments, a fast Sel-MQC sequence with a spiral k-space sampling scheme was demonstrated to selectively detect PUFA or MUFA signals in tissues containing high fat concentration. Spiral-SelMQC maps of PUFA distributions in human breast tissues were obtained in vivo with approximately 160-fold imaging time reduction compared to Sel-MQC CSI experiment with an equivalent number of scans. Thus, fast spectroscopic imaging techniques may be applied for time-resolved acquisitions to study metabolic processes in human breast cancer or other human diseases, even in extracranial organs where traditional MRSI techniques have been unsuccessful. Spiral parameters can be optimized using 2D techniques such as those associated with systems and methods discussed herein to suppress signals of chemicals to be filtered (e.g., MUFA and other non-target lipid and water signals). Metabolites with coupled spins (e.g., lactate) or antineoplastic agents may be imaged similarly within a clinical time limit. The effective selection of PUFA, MUFA, or metabolite signals depends on their chemical shift differences at high field MRI systems (>2.1T). Although the specific example of the Spiral-SelMQC technique has been discussed herein, other fast data acquisition techniques may also be employed—e.g., Spiral-SelZQC techniques, or echo-planar methods that may be applied to detect multiple metabolites simultaneously in association with methods or systems described herein. On modern MRI scanners equipped with multiple coil array devices, SENSE, SMASH, and GRAPPA or other parallel imaging techniques may be employed in spectroscopic imaging such as the systems and methods described herein to further improve spatial and temporal resolution of PUFA and metabolite mapping in human breast tissues or other extracranial organs with complete suppression of non-target lipid and water signals.

Various techniques described herein, for example, the fast MRSI techniques, may be automated to streamline implementation of the systems and methods. For example, particular selections of molecules and corresponding parameters can be pre-determined so as to reduce computational and analytic requirements in a clinical setting while providing high-quality and rapid data acquisition. Multiple sequences can be determined and prepared ahead of time so as to provide diagnostic options for the detection of specific chemicals (e.g., metabolic markers, drugs, etc.) in an accessible format, for example, through a graphical user interface.

As discussed in greater detail next, system(s) and method(s) for magnetic resonance imaging and spectroscopy, and magnetic resonance spectroscopic imaging (MRSI) are provided. Aspects of the subject innovation can be performed with a single coil system, or with a heteronuclear coil system as described in the following systems and methods. An NMR spectrometer used for MRS or MRSI can include some or all of: a magnet to produce the $B_0$ field (generally superconducting, although permanent magnets or non-superconducting electromagnets can be used), a probe that can enable a coil or coils to excite and detect the signal (the coils can form part of a tuned circuit that can be adjusted to various Larmor frequencies), an RF transmitter that can deliver pulses, a receiver that can amplify received signals, a digitizer that can convert received signals from analog to digital signals, a pulse programmer that can coordinate timing of pulses and delays, and a computer that can control the other components and can process received data. Additionally, although homonuclear (e.g., $^1H$) techniques can be employed with systems and methods discussed herein, in other aspects, detection techniques can also employ heteronuclear techniques, as described below.

These systems and methods also can be used in conjunction with other systems and methods of the subject innovation, for example, to provide for MRSI data acquisition and calibration in connection with systems or methods employing sequences discussed herein. A unified heteronuclear coil system can include a volume coil tuned to detect a first nuclei and a butterfly coil tuned to detect a second nuclei for simultaneous detection of both the first nuclei and the second signals from tissue (e.g., human breast tissue) and perform MRSI. First nuclei and second nuclei can each include at least $^1H$, $^{13}C$, $^{31}P$, $^{23}Na$, and $^{19}F$, as well as other nuclei, for example nuclei used in contrast agents. The heteronuclear coil system can afford detection of nuclear magnetic resonance (NMR)-detectable chemicals specific to cancerous tissue to improve cancer diagnostic specificity. Adjustment of the heteronuclear coil system to detect various nuclei, combined with a specific pulse excitation sequence, can facilitate chemical analysis that can provide for chemical discrimination and characterization of compounds present in cancerous and other tissue (e.g., breast tissue) as well as healthy physiology (e.g., breast physiology).

Figure 15:
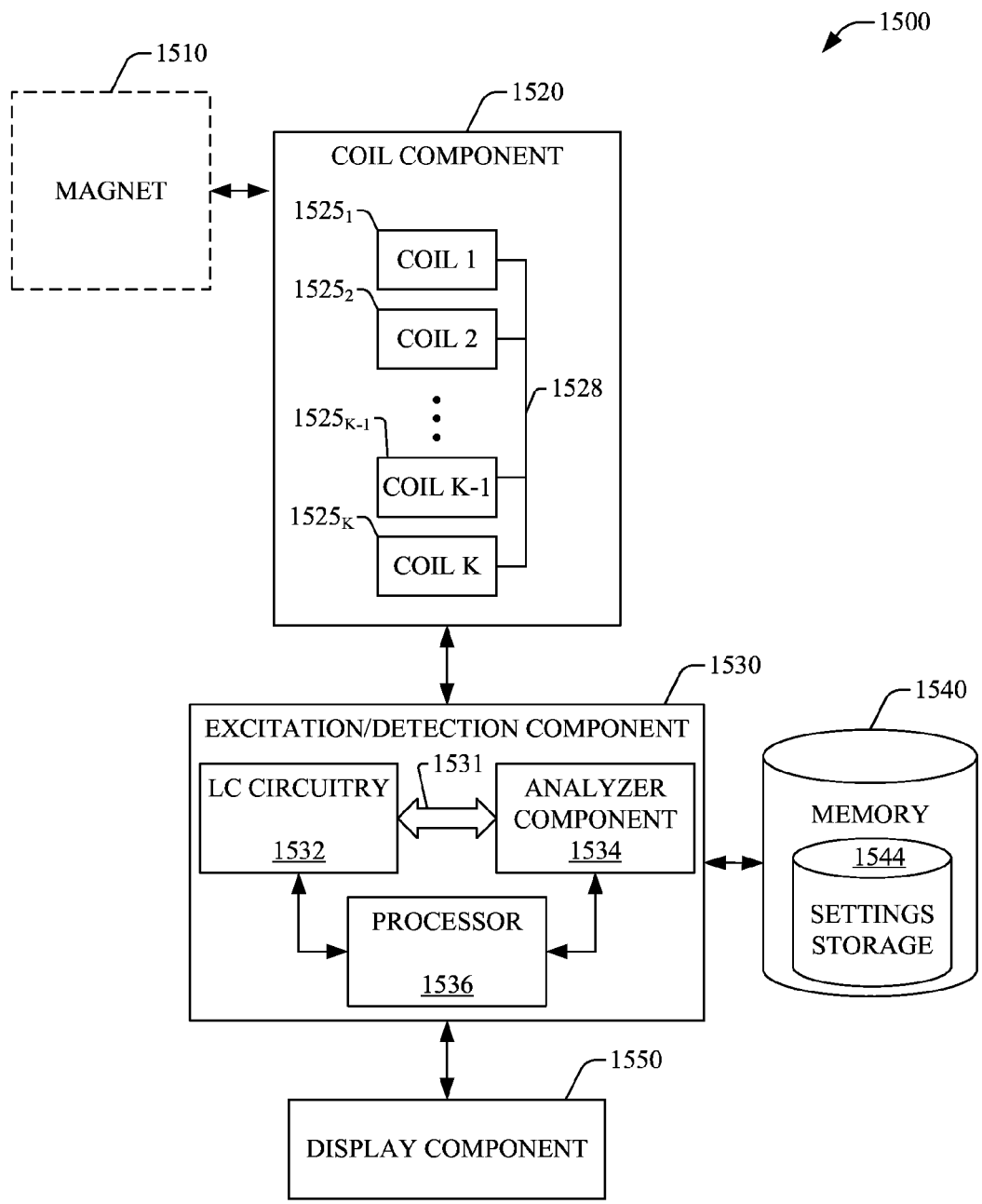
FIG. 15 shows an example magnetic resonance system useable in connection with aspects of the subject innovation.

FIG. 15 is an example system that can facilitate chemical analysis of soft tissue (e.g., breast tissue, muscle or joint tissue) disease through a combination of a coil system (e.g., one or more coils, where a multiple coil system can employ separate transmit and receive coils, and/or employ a heteronuclear coil system, quadrature coil system, etc.) with magnetic resonance spectroscopy (MRS) or imaging (MRI), or magnetic resonance spectroscopic imaging (MRSI) methods. Chemical analysis can include monitoring chemical changes in tissue indicative of cancerous tissue, such as decreased levels of polyunsaturated fatty acids (PUFAs), by selectively detecting certain chemicals that contain the one or more nuclei for which the coil system has been designed. Detection can target the presence of NMR-detectable chemicals specific to cancerous tissue (e.g., cancerous breast tissue) to improve cancer diagnostic specificity. Additionally, a coil system can be used generally for other diseases and studying healthy and abnormal physiology in vivo. It should be appreciated that other chemicals can be monitored as indicators of cancer or other conditions. In a heteronuclear embodiment, the heteronuclear sensitivity of a heteronuclear coil system tuned to $^1H/^{13}C$ nuclei (or others, such as one or more of at least $^1H$, $^{13}C$, $^{31}P$, $^{23}Na$, and $^{19}F$), for example, can be used to study carbon signals from disparate, abundant molecules in healthy and cancerous tissues, including anti-cancer drugs. As indicated above, variations and similarities in local geometry in molecules can cause variations in chemical shift, leading to spectra for molecules. These spectra can be used to determine the structure of or detect the presence of molecules.

A heteronuclear coil system, with suitable $N_A/N_B$ combinations of nuclei sensitivity, can be employed for chemical analysis of lipids and metabolites in vivo, like the glucose molecule and its metabolic products, polyunsaturated fatty acids, etc. Additionally, the heteronuclear coil system can be modified to observe substantially any NMR sensitive nuclei in addition to $^1H$ and $^{13}C$, such as sodium signals ($^{23}Na$), fluorine signals ($^{19}F$) in anti-cancer drugs such as 5-FU, and phosphorous ($^{31}P$) signals, which were the first NMR modality signals to demonstrate that MRS can detect tumor metabolites that are different from normal tissues.

Generally, chemical structure, chemical content, and chemical reactivity can be discriminated with a heteronuclear coil system based on chemical bonding. Chemical reactions between drugs and cancerous tissue can be monitored by a suitable choice of nuclei $N_A$ and $N_B$. It is noted that more comprehensive combinations of nuclei can be established in heteronuclear coil systems that include more than two coils, or heteronuclear coil systems with multi-tuned constituent coils. Similarly, chemical interaction between compounds in cancerous and healthy tissue can be analyzed, as can the chemical reactivity of a compound in healthy tissue and cancerous tissue. It should be appreciated that chemical analysis can be helpful to understanding cancer (e.g., breast cancer) in view of the variety of metabolic changes expressed from individual to individual.

In an aspect of the subject innovation, chemical characterization as described herein can be directed not only to diagnosis of soft tissue (e.g., breast tissue, joint tissue) disease(s) but it can be directed to monitoring treatment thereof. Regarding treatment, chemical characterization through MRSI as described in the subject innovation can be employed to monitor efficacy of a treatment regimen by detecting the biochemical activity of a tumor or other condition. Generally, when a treatment drug is going to be therapeutically effective, biochemical activity (e.g., of a target tumor in a cancer setting) changes shortly after implementation of the treatment drug. Thus, chemical characterization via MRSI can provide almost immediate feedback in connection with treatment effectiveness, which can allow physicians to switch medications (e.g., treatment drugs) when a current medication fails to show improvement in connection with attacking the tumor, etc. A similar approach can be employed with any other soft tissue disease to which treatment drugs are directed. At least one advantage of such expedited feedback provided by the subject innovation is that decision-making time regarding change(s) from an ineffective drug to an effective drug can be greatly reduced, with the ensuing increase in treatment outcomes.

To conduct chemical analysis and MRI, example system 1500 can comprise a magnet 1510 that can provide an external field ($B_0$) and a coil component 1520 (which can be a heteronuclear or quadrature coil component that can be used as part of a heteronuclear or quadrature coil system, if it comprises more than one coil) that can include a set of K coils $1525_1$-$1525_K$ (where K is a positive integer) that can provide sensitivity to one or more nuclei. Coils $1525_1$-$1525_K$ can be magnetically decoupled but functionally coupled through a coupling element 1528; the coupling element can facilitate mechanical coupling, electrical coupling, electronic coupling, electromagnetic coupling, or any combination thereof. Such coupling can be adjusted for operational selectivity, e.g., selection of a pair of coils that are active in order to determine measurement(s). Coils $1525_1$-$1525_K$ can include any of a variety of coils, such as volume coils and butterfly coils. In addition, for K greater than one, the set of K coils can be employed as a multi-coil array system for excitation/detection, wherein a first subset of the set of coils can include transmitter coils and a second subset can include receiver coils. Each coil in either subset can be driven by a single channel in an excitation/detection component (e.g., component 1530). As an example, for K=2, coil component can employ a butterfly coil and a volume coil for chemical discrimination, based upon chemical shift profiles measured through NMR. Example system 1500 can include an excitation/detection component 1530 coupled to a settings storage 1544 that resides within a memory 1540. In addition, example system 1500 includes a display component 1550 for analysis and manipulation of data.

Excitation/detection component 1530 can include LC circuitry 1532 which can include RF matching/tuning circuitry, which can be employed to automatically tune to one or more resonance Larmor frequencies for one or more selected nuclei at the operation external magnetic field ($B_0$) provided by magnet 1510. In addition, component 1530 can include RF electronics, e.g., included within LC circuitry 1532, to generate a sequence of applied pulses (e.g., $\pi/2$ (90°) and $\pi$ (180°) pulses), which can include application of multiple pulses at specific time intervals such as TE and TR, in order to accomplish specific coherent excitation of nuclear spin targets for monitoring and detection of spin dynamics. As an example, predetermined excitation sequences such as selective single, multiple quantum coherence (Sel-MQC) or zero-quantum coherence (Sel-ZQC), or substantially any other sequence, as well as parameters relevant to MRSI experiments in particular microscopic parameters associated with probed nuclei (e.g., spin-spin coupling constants, relaxation times ($T_1$) or decoherence times ($T_2$), echo times, repetition times) can be stored in settings storage 1544. Excitation/detection component 1530, through analyzer component 1534, can determine slices (e.g., axial, coronal, or sagittal, etc.) for probing intracranial or extracranial tissue (e.g., a human breast, or other organs) and can also process data according to a selected algorithm (e.g., $T_1$-weighting or $T_2$-weighting).

In various embodiments, LC circuitry 1532 can be functionally coupled to an analyzer component 1534 through a link component 1531 (e.g., coaxial cable, etc.). In an aspect, analyzer component 1534 can include a network analyzer that can facilitate characterization of coil (e.g., coil $1525_2$, or any other coil) resonance features. Analyzer component 1534 can allow direct determination of the coil quality factor (Q) and estimation of a return-loss factor for the coil. In addition, analyzer component 1634 can facilitate, via a Smith chart, etc., assessment of actual inductance and capacitance in the LC circuitry that includes the coils. Moreover, a Smith chart can facilitate adjusting the impedance between LC circuitry 1532 and analyzer component 1534. It should be appreciated that LC circuitry 1532 can include one or more of coils $1525_1$-$1525_K$.

Processor 1536 can confer, at least in part, functionality to one or more components of example system 1500. In an aspect, processor 1536 can execute code instructions in software or firmware in order to provide components with their specific functionality; e.g., a processor can execute code instructions to generate sequences described herein (e.g., Sel-ZQC or CS-SelZQC sequences, etc.), or any other sequence, utilized to excite one or more coils within coil component 1520. Memory 1540 can retain the code instructions in software or firmware that processor 1536 can execute. In addition, memory 1540 can retain settings storage that includes microscopic parameters associated with operation of coil component 1520 and substantially any component in example system 1500.

Systems and methods described herein can be used in conjunction with other MRI, MRS, and MRSI techniques. Different sequences and techniques discussed herein can improve sequences described here and can determine the relaxation times of edited signals for tissue metabolite quantification (e.g., lactate and other signals). The subject innovation can be used in connection with other techniques, such as volume selective techniques using "1331" composite pulses, a multi-slice method for 3D mapping of metabolites using the Hadamard matrix approach, or a 3D spectroscopic imaging technique using spatial-spectral (SPSP) selective radio frequency (RF).

In accordance with aspects of the innovation, modified sequences for simultaneous detection of one or more sets of chemicals in different multiple quantum coherence transfer pathways have been developed, which can be used in conjunction with double spin-echo methods such as double-spin echo enhanced (DSE) versions of sequences described herein for simultaneous detection of one or more chemicals through spin-echo pathways (e.g., choline) along with other chemicals of interest (e.g., lactate, PUFA, etc.). In various embodiments discussed herein, pulse sequences are discussed that permit simultaneous detection of PUFA, lactate and choline in tissues containing high concentration of mobile lipid, with complete suppression of water and non-target lipid resonances in a single scan.

The subject innovation described herein can provide multiple advantages. One advantage is the ability to accurately detect target chemicals in high or ultrahigh magnetic field, even in situations involving magnetic field inhomogeneities, susceptibility effects, or high concentrations of non-target chemicals (e.g., water, lipid, etc.). A further advantage is high detection sensitivity and RF field homogeneity as compared to conventional coil systems to detect cancer-specific biochemicals (e.g., related to breast cancer) containing at least proton ($^1$H), fluorine-19 ($^{19}$F), carbon-13 ($^{13}$C), sodium-23 ($^{23}$Na), phosphorous-31 ($^{31}$P) nuclei. Another advantage is a broad chemical shift range for spectroscopic editing with utilization of homonuclear and heteronuclear sequences at high and/or ultrahigh magnetic field, which permits detection of potential cancer-specific markers (e.g., breast cancer markers) unavailable conventionally. When utilized with $^{13}$C hyper-polarization sequence, a heteronuclear coil system of the subject innovation may map tumor enzyme activities for cancer detection, resulting in improved diagnostic specificity to differentiate malignant tumors. Additionally, this innovation can provide diagnosis of soft tissue (e.g., breast tissue, joint tissue) disease(s) or monitoring of treatment thereof.

Although the potential applications discussed in the foregoing have largely focused on cancer (e.g., detection of chemical markers and monitoring of treatment) because of the high demand for improved techniques in that arena and the shortcomings of traditional methods, systems and methods of the subject innovation can be employed in a wider range of settings, as well. Embodiments of the present innovation can be employed in any setting involving MRSI that involves overlapping signals, by using the systems and methods described herein to perform spin editing in order to remove non-target signals while retaining signals of interest. In particular examples, these systems and methods can be used to image or monitor transplants or artificial organs. Additional applications include tissue engineering, grown tissues, and stem cell research (as well as potential future therapeutic applications), where these systems and methods can be used to monitor the development of tissue biochemically to distinguish between healthy growth and tumors. In addition, other advantages would be apparent to a person of skill in the art in light of the discussion herein.

As it employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions or acts described herein. A processor may also be implemented as a combination of computing processing units, which can be distributed or deployed in a single location or environment.

In the subject specification, the term "memory" can refer to data stores, algorithm stores, and substantially any other information store relevant to operation and functionality of a component or system comprising the memory; for instance, such information can include excitation pulse sequences, capacitance values to tune a coil system to probe a specific nuclei, microscopic nuclei parameters relevant to MRSI such as computed or measured relaxation times and decoherence times, and so forth. It will be appreciated that the memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method; apparatus, either as hardware or hardware and software or firmware; or article of manufacture using standard programming and/or engineering techniques. Implementation(s) that include software or firmware can be effected at least in part through program modules stored in a memory and executed by a processor. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical discs (e.g., compact disk (CD), digital versatile disc (DVD), Blu-ray disc (BD) . . . ), smart cards, and flash memory devices (e.g., card, stick, key drive . . . ).

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of detecting magnetic resonance (MR) signals, comprising:
    exciting a set of target chemicals into a set of multiple-quantum (MQ) states;
    applying a gradient pulse to select zero-quantum coherences (ZQCs) of the set of target chemicals;
    converting the ZQCs into a set of detectable magnetizations; and
    acquiring signals from the set of target chemicals during an acquisition period.

2. The method of claim 1, wherein acquiring signals from the set of target chemicals comprises acquiring a ZQ cross peak of the set of target chemicals via taking multiple measurements over time based on incrementation in a ZQ-evolution period.

3. The method of claim 1, further comprising:
    applying a plurality of gradient pulses to suppress signals from a set of non-target chemicals.

4. The method of claim 3, wherein the set of non-target chemicals comprises one or more of water or a lipid.

5. The method of claim 3, wherein the plurality of gradient pulses comprise a double quantum filter (DQF) wherein a first gradient pulse of the plurality of gradient pulses and a second gradient pulse of the plurality of gradient pulses are in a ratio of −1 to 2.

6. The method of claim 1, wherein the set of target chemicals comprises one or more of a polyunsaturated fatty acid, lactate, or an antineoplastic agent.

7. The method of claim 1, wherein converting the ZQCs into a set of detectable magnetizations comprises:
    converting the ZQCs into double quantum conherences (DQCs) of the set of target chemicals; and
    converting the DQCs into a single-quantum (SQ) magnetization of the set of target chemicals.

8. The method of claim 1, further comprising applying a frequency encoding gradient and a phase encoding gradient to the set of target chemicals, or a set of 2D- or 3D-gradients for fast k-space mapping.

9. The method of claim 1, wherein exciting the set of target chemicals into the set of MQ states comprises:
applying a first selective pulse to a first set of nuclei of the set of target chemicals; and
applying a second selective to a second set of nuclei of the set of target chemicals after an MQ preparation period.

10. A magnetic resonance spectroscopic imaging (MRSI) system, comprising:
a sample that comprises one or more target chemicals and one or more non-target chemicals;
a magnet that applies a $B_0$ field to the one or more target chemicals and the one or more non-target chemicals;
an excitation/detection component that generates a sequence of pulses that excites the one or more target chemicals into a first set of multiple-quantum (MQ) states, selects a zero-quantum coherence (ZQC) of the one or more target chemicals, and converts the one or more target chemicals from the ZQC to a detectable magnetization, and wherein the excitation/detection component acquires signals from the one or more target chemicals during an acquisition period.

11. The system of claim 10, wherein the excitation/detection component acquires a ZQ cross peak of the one or more target chemicals via incrementation in a ZQ-evolution period.

12. The system of claim 10, wherein the excitation/detection component suppresses signals from one or more non-target chemicals.

13. The system of claim 12, wherein the one or more non-target chemicals comprises one or more of water or a lipid.

14. The system of claim 12, wherein the excitation/detection component employs a double quantum filter (DQF) gradient to suppress the signals from the one or more non-target chemicals, wherein the DQF gradient comprises two gradient pulses $g_1$ and $g_2$ in the ratio $g_1:g_2 = -1:2$.

15. The system of claim 10, wherein the one or more target chemicals comprises one or more of a polyunsaturated fatty acid, lactate, or an antineoplastic agent.

16. The system of claim 10, wherein the excitation/detection component converts the one or more target chemicals to the detectable magnetizations via a double quantum coherence (DQC) of the one or more target chemicals.

17. The system of claim 10, wherein the excitation/detection component applies a frequency encoding gradient and a phase encoding gradient to the one or more target chemicals, or a 2D- or 3D gradient for fast k-space mapping.

18. The system of claim 10, further comprising:
a processor that analyzes a spin coupling network of the one or more target chemicals to determine one or more resonance frequencies of the one or more target chemicals and one or more scalar coupling constants associated with the one or more target chemicals, wherein the one or more frequency offsets of the one or more RF pulses are determined based at least in part on the one or more scalar coupling constants associated with the one or more known molecules.

19. A magnetic resonance spectroscopic imaging (MRSI) system, comprising:
means for producing a $B_0$ field that acts on a sample that contains a set of target molecules;
means for exciting the set of target molecules into a set of multiple-quantum (MQ) states, wherein the means for exciting further applies a zero-quantum coherence (ZQC) selection gradient pulse to convert the set of target molecules to a zero-quantum (ZQ) mode, and wherein the means for exciting converts the set of target molecules to a single-quantum (SQ) magnetization via a double-quantum coherence (DQC) of the set of target molecules; and
means for acquiring signals from the set of target molecules during an acquisition period.

20. The system of claim 19, wherein the means for acquiring acquires a ZQ cross peak of the set of target molecules via multiple measurements taken by incrementation in a ZQ-evolution period in two-dimensional magnetic resonance (2D-MRS) spectra and imaging.

* * * * *